US011478336B1

(12) United States Patent
Shao

(10) Patent No.: US 11,478,336 B1
(45) Date of Patent: Oct. 25, 2022

(54) ORTHODONTIC APPLIANCES

(71) Applicant: Sympal, Inc., Bedford, MA (US)

(72) Inventor: Cheryl B. Shao, Bedford, MA (US)

(73) Assignee: Sympal, Inc., Bedford, MA (US)

(*) Notice: Subject to any disclaimer, the term of this patent is extended or adjusted under 35 U.S.C. 154(b) by 0 days.

(21) Appl. No.: 17/526,815

(22) Filed: Nov. 15, 2021

(51) Int. Cl.
A61C 7/00 (2006.01)
A61C 7/08 (2006.01)
A61C 9/00 (2006.01)
A61C 7/10 (2006.01)

(52) U.S. Cl.
CPC ............... A61C 7/08 (2013.01); A61C 7/002 (2013.01); A61C 7/10 (2013.01); A61C 9/0046 (2013.01); A61C 2007/004 (2013.01)

(58) Field of Classification Search
CPC .. A61C 7/08; A61C 7/002; A61C 7/10; A61C 9/0046; A61C 2007/004
See application file for complete search history.

(56) References Cited

U.S. PATENT DOCUMENTS

| 4,755,139 A | 7/1988 | Abatte et al. |
| 4,798,534 A | 1/1989 | Breads |
| 4,815,968 A | 3/1989 | Keller |
| 4,856,991 A | 8/1989 | Breads et al. |
| 5,035,613 A | 7/1991 | Breads et al. |
| 5,055,039 A | 10/1991 | Abbatte et al. |
| 5,059,118 A | 10/1991 | Breads et al. |
| 5,186,623 A | 2/1993 | Breads et al. |
| 5,605,459 A | 2/1997 | Kuroda et al. |
| 5,829,970 A | 11/1998 | Yousefian |
| 6,702,575 B2 | 3/2004 | Hilliard |
| 6,790,036 B2 * | 9/2004 | Graham ................... A61C 7/08 128/859 |

(Continued)

FOREIGN PATENT DOCUMENTS

| WO | 9858596 A1 | 12/1998 |
| WO | 01/80762 A2 | 11/2001 |

OTHER PUBLICATIONS

Mew Indicator Line: Maxilla Positioning by Prof. John Mew—Mewingpedia, downloaded Feb. 23, 2022, available at https://mewingpedia.com/mew-indicator-line-maxilla-positioning-by-prof-john-mew/.

Primary Examiner — Nicholas D Lucchesi
(74) Attorney, Agent, or Firm — Gordon & Jacobson, P.C.

(57) ABSTRACT

Methods and systems are provided repositioning teeth of a patient, which employ at least one appliance specific to the patient for placement in the patient's mouth during use. The at least one appliance includes a polymeric shell having a cavity shaped to receive teeth of the upper jaw of the patient. The polymeric shell is integral to a polymeric segment shaped to cover the hard palate of the upper jaw of the patient. The geometry and material properties of the shell is configured such that the appliance adjusts position of the teeth of the upper jaw of the patient during use. The geometry and material properties of the segment is configured such that the appliance adjusts position of the hard palate of the upper jaw of the patient during use. Additionally or alternatively, one or more appliances can be configured to contact the teeth of the lower jaw and a mandibular bone portion disposed below the gingiva of the teeth of lower jaw and adjust position of the teeth and the mandibular bone portion of the lower jaw of the patient during use.

26 Claims, 18 Drawing Sheets

(56) References Cited

U.S. PATENT DOCUMENTS

| | | |
|---|---|---|
| 7,273,367 B2 | 9/2007 | Hughes et al. |
| 3,062,031 A1 | 11/2011 | Inman |
| 8,060,236 B2 | 11/2011 | Hilliard |
| 9,610,141 B2 | 4/2017 | Kopelman et al. |
| 9,655,693 B2 | 5/2017 | Li et al. |
| 2002/0192617 A1 | 12/2002 | Phan et al. |
| 2003/0224311 A1 | 12/2003 | Cronauer |
| 2004/0009449 A1 | 1/2004 | Mah et al. |
| 2004/0096799 A1 | 5/2004 | Hughes et al. |
| 2004/0209218 A1 | 10/2004 | Chishti et al. |
| 2005/0069834 A1 | 3/2005 | Inman |
| 2005/0100857 A1* | 5/2005 | Skarky ............... A61C 9/00 433/70 |
| 2007/0087300 A1 | 4/2007 | Willison et al. |
| 2008/0020337 A1 | 1/2008 | Phan et al. |
| 2009/0142723 A1 | 6/2009 | Govaert |
| 2011/0020761 A1 | 1/2011 | Kalili |
| 2014/0170585 A1 | 6/2014 | Parker |
| 2015/0125802 A1 | 5/2015 | Tal |
| 2015/0245887 A1* | 9/2015 | Izugami ............... A61C 7/36 433/6 |
| 2016/0081768 A1* | 3/2016 | Kopelman ............ A61C 7/10 433/6 |
| 2016/0081769 A1* | 3/2016 | Kimura ............... A61C 7/10 433/6 |
| 2017/0007366 A1* | 1/2017 | Kopelman ............ A61C 7/10 |
| 2018/0153648 A1* | 6/2018 | Shanjani ............. A61C 7/08 |
| 2018/0153649 A1* | 6/2018 | Wu ................. G16H 40/67 |
| 2018/0185188 A1* | 7/2018 | Lamberg ............. A61F 5/566 |
| 2018/0368944 A1* | 12/2018 | Sato ................ A61C 7/10 |
| 2019/0021817 A1* | 1/2019 | Sato ................ A61C 7/14 |
| 2019/0152152 A1* | 5/2019 | O'Leary ............ B33Y 50/00 |
| 2019/0262101 A1* | 8/2019 | Shanjani ............ A61C 7/36 |
| 2019/0314119 A1* | 10/2019 | Kopelman ......... A61C 7/023 |
| 2021/0147672 A1* | 5/2021 | Cole ............... B33Y 70/00 |
| 2021/0220087 A1* | 7/2021 | Kopelman ......... B33Y 80/00 |

\* cited by examiner

ORTHODONTIC APPLIANCES

BACKGROUND

1. Field

The present disclosure relates generally to the field of orthodontics and, more particularly, to computer-aided design and manufacture of appliances for orthodontic adjustment of a patient's upper and lower jaw.

2. Background Art

Repositioning teeth for aesthetic or other reasons is accomplished conventionally by wearing "braces," which comprise of a variety of appliances such as brackets, arch wires, ligatures, and O-rings. Attaching the appliances to a patient's teeth is a tedious and time consuming enterprise requiring many meetings with the treating orthodontist.

Alternative methods and systems for repositioning teeth have been developed and commercialized that employ clear polymeric aligners that fit over the teeth of the patient. The aligners are designed and fabricated through the use computer-aided technology to apply desired corrective forces to the teeth when worn. Examples of such methods and systems are described in PCT Publ. No. WO1998058596 and U.S. Pat. No. 7,273,367.

Tooth positioners for finishing orthodontic treatment are described by Kesling in Am. J. Orthod. Oral. Surg. 31:297-304 (1945) and 32:285-293 (1946). The use of silicone positioners for the comprehensive orthodontic realignment of a patient's teeth is described in Warunek et al. (1989) J. Clm. Orthod. 23:694-700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4, 755, 139. Other publications describing the fabrication and use of dental positioners include Kleemann and Janssen (1996) J. Clm. Orthod. 30:673-680, Cureton (1996) J. Clm. Orthod. 30.390-395, Chiappone (1980) J. Clm. Orthod. 14.121-133; Shilliday (1971) Am. J. Orthodontics 59:596-599; Wells (1970) Am. J. Orthodontics 58:351-366; and Cottingham (1969) Am. J. Orthodontics 55:23-31.

Kuroda et al. (1996) Am. J. Orthodontics 110:365-369 describes a method for laser scanning a plaster dental cast to produce a digital image of the cast. See also U.S. Pat. No. 5,605,459.

SUMMARY

In one aspect, methods and systems are provided for repositioning teeth of a patient, which employ at least one appliance (i.e., "top aligner") specific to the patient for placement in the patient's mouth during use. The at least one appliance includes a polymeric shell having a cavity shaped to receive teeth of the upper jaw of the patient. The shell is integral to a polymeric segment shaped to cover the hard palate of the upper jaw of the patient. The geometry of the shell is configured such that the appliance adjusts position of the teeth of the upper jaw of the patient during use. The geometry of the segment is configured such that the appliance adjusts position of the hard palate of the upper jaw of the patient during use.

In embodiments, the at least one appliance specific to the patient includes a plurality of appliances specific to the patient which are used in a predefined order by the patient. Specifically, the plurality of appliances can be configured to progressively adjust position of the teeth and hard palate of the upper jaw of the patient.

In embodiments, the geometry of the segment and the geometry of the shell for a particular appliance are derived from a three-dimensional model of the surfaces of the teeth and hard palate of the upper jaw of the patient. The three-dimensional model can be used to generate a physical model of the surfaces of the teeth and hard palate of the upper jaw of the patient. The physical model can be used as mold to form the particular appliance.

In embodiments, the three-dimensional model of the surfaces of the teeth and hard palate of the upper jaw of the patient can be generated by isolating a part or segment of a three-dimensional model which corresponds to surfaces of the hard palate of the upper jaw of the patient, and moving or stretching or otherwise transforming the isolated part of the three-dimensional model. Such moving or stretching or otherwise transforming the isolated part of the three-dimensional model can involve translation or rotation or other movement of the isolated part of the three-dimensional model relative to a reference coordinate system defined in the three-dimensional model.

In embodiments, the geometry of the shell can be configured such that the appliance expands the teeth of the upper jaw of the patient during use, and the geometry of the palate segment can be configured such that the appliance moves the hard palate upward and forward during use.

The methods and systems can employ at least one additional appliance (i.e., "bottom aligner") specific to the patient for placement in the patient's mouth during use. The at least one additional appliance includes a polymeric shell having a cavity shaped to receive teeth of the lower jaw of the patient. The geometry of the shell is configured such that the appliance adjusts position of the teeth of the lower jaw of the patient during use. The at least one additional application can include a polymeric segment that is integral to the shell and configured to contact a mandibular bone portion disposed below the gingiva of the teeth of lower jaw. The geometry of this segment can be configured such that the appliance adjusts position of the mandibular bone portion of the lower jaw of the patient during use.

In embodiments, the geometries of the shell and segment for a particular additional appliance can be derived from a three-dimensional model of the surfaces of the teeth and mandibular bone portion of the lower jaw of the patient.

In embodiments, the at least one additional appliance specific to the patient includes a plurality of additional appliances specific to the patient which are used in a predefined order by the patient. Specifically, the plurality of additional appliances can be configured to progressively adjust position of the teeth and mandibular bone portion of the lower jaw of the patient.

In another aspect, a method is provided for producing a 3D model representing a desired arrangement of the surfaces of the teeth and hard palate of the upper jaw of a patient. The method can include the steps of:
- generating an initial three-dimensional model representing surfaces of the teeth and hard palate of the upper jaw of a patient;
- isolating a tooth portion of the initial three-dimensional model which corresponds to surfaces of at least one tooth of the upper jaw of the patient;
- moving the tooth portion;

isolating a palate portion of the initial three-dimensional model which corresponds to surfaces of the hard palate of the upper jaw of the patient; and moving or stretching or otherwise transforming the palate portion.

The palate portion can correspond to surfaces of all or part of the hard palate of the upper jaw of the patient.

In embodiments, the moving or stretching or otherwise transforming the palate portion involves distortion, translation or rotation or other movement of the palate portion relative to a reference coordinate system defined in the initial three-dimensional model.

In another aspect, a method is provided for producing a 3D model representing a desired arrangement of the surfaces of the teeth and bone of the lower jaw of a patient. The method can include the steps of:

generating an initial three-dimensional model representing surfaces of the teeth and a mandibular bone portion disposed below the gingiva of the lower jaw of a patient;

isolating a tooth portion of the initial three-dimensional model which corresponds to surfaces of at least one tooth of the lower jaw of the patient:

moving the tooth portion;

isolating a mandibular bone part of the initial three-dimensional model which corresponds to surfaces of the mandibular bone portion of the lower jaw of the patient; and moving or stretching or otherwise transforming the mandibular bone part.

The mandibular bone part can correspond to surfaces representing a section or part of the mandibular bone structures of the lower jaw of the patient.

In embodiments, the moving or stretching or otherwise transforming the mandibular bone part involves distortion, translation or rotation or other movement of the mandibular bone part relative to a reference coordinate system defined in the initial three-dimensional model.

DETAILED DESCRIPTION OF THE PREFERRED EMBODIMENTS

Figure 1A:
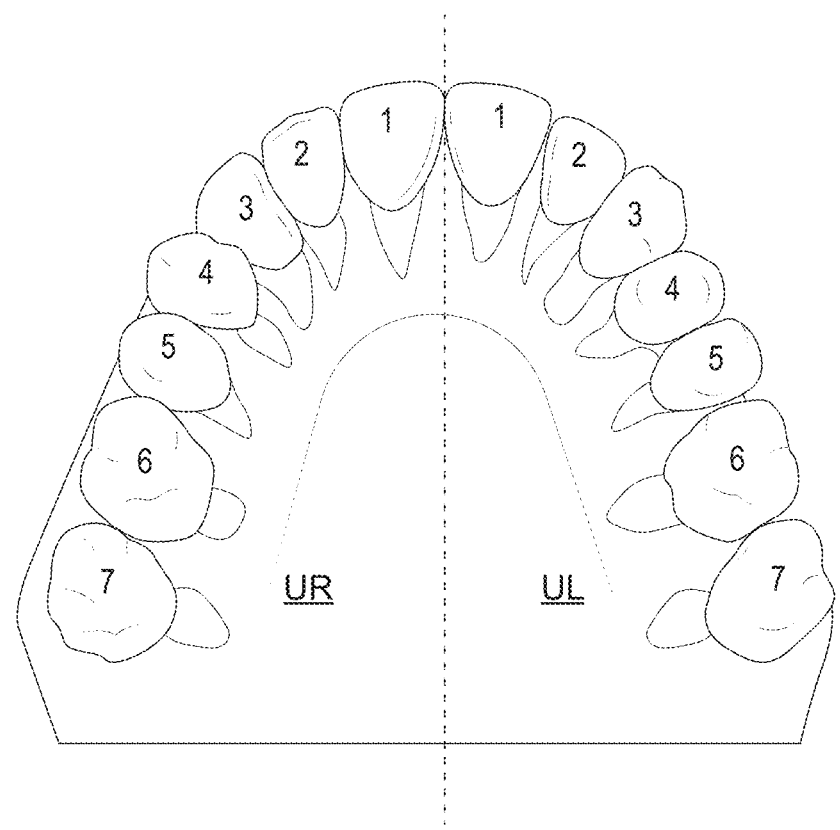
FIG. 1A is an X-ray image of the teeth and hard palate of the upper jaw of a human being.

FIG. 1A depicts the teeth of the upper jaw or maxilla of a human being, which includes seven teeth on the right side (i.e., upper right quadrant labeled "UR") of the upper jaw labeled 1 (central incisor), 2 (lateral incisor), 3 (canine), 4 (first premolar), 5 (second premolar), 6 (first molar) and 7 (second molar) as well as seven teeth on the left side (i.e., upper left quadrant labeled "UL") of the upper jaw labeled 1 (central incisor), 2 (lateral incisor), 3 (canine), 4 (first premolar), 5 (second premolar), 6 (first molar) and 7 (second molar).

Figure 1B:
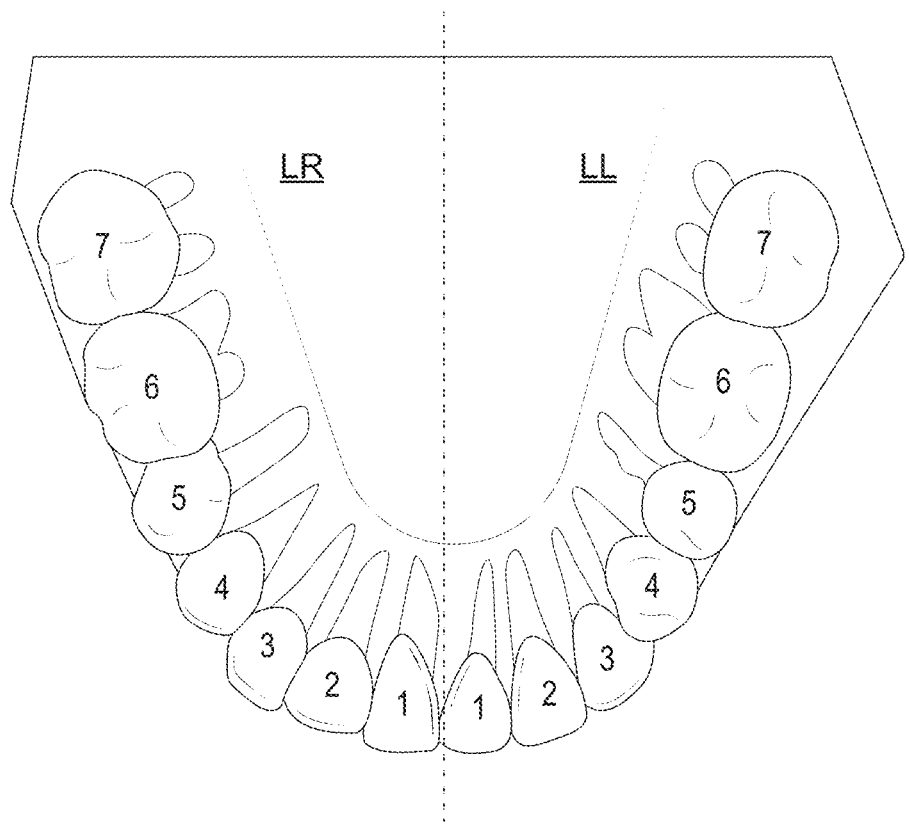
FIG. 1B is an X-ray image of the teeth of the lower jaw of a human being.

FIG. 1B depicts the teeth of the lower jaw or mandible of a human being, which includes seven teeth on the left side (i.e., lower left quadrant labeled "LL") of the lower jaw labeled 1 (central incisor), 2 (lateral incisor), 3 (canine), 4 (first premolar), 5 (second premolar), 6 (first molar) and 7 (second molar) as well as seven teeth on the right side (i.e., lower right quadrant labeled "LR") of the lower jaw labeled 1 (central incisor), 2 (lateral incisor), 3 (canine), 4 (first premolar), 5 (second premolar), 6 (first molar) and 7 (second molar).

Figure 2A:
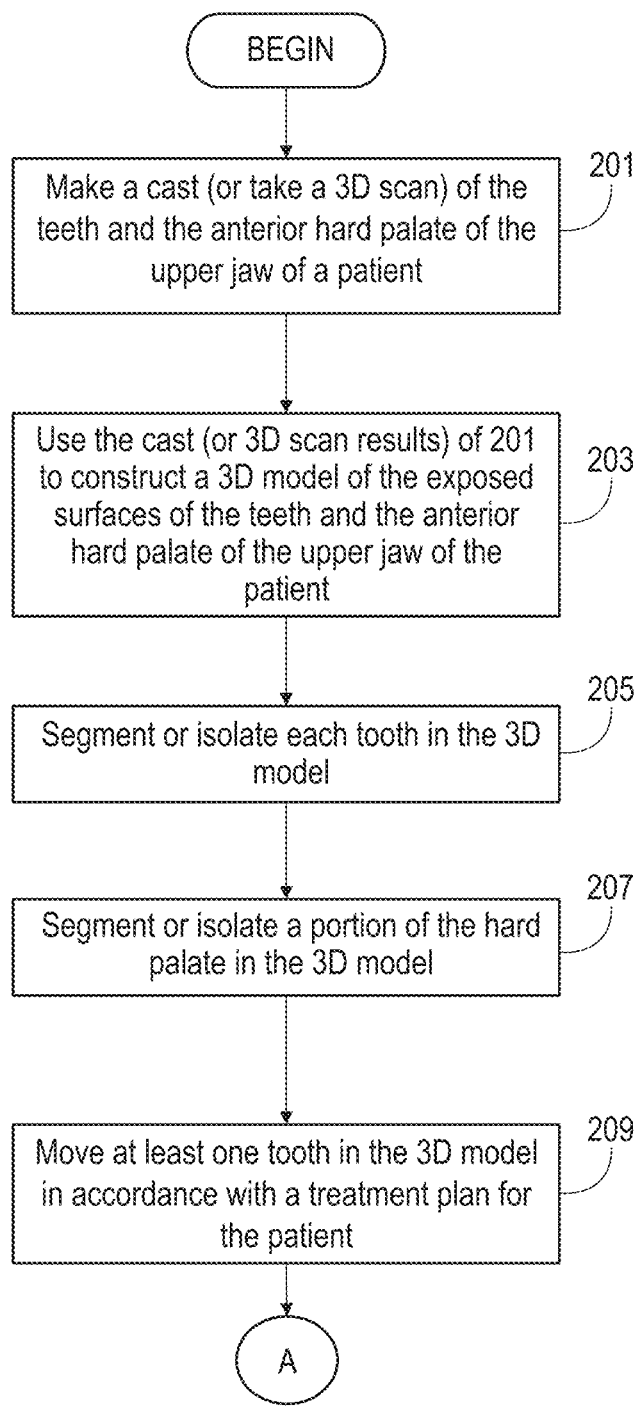
FIGS. 2A to 2B, collectively, is a flow chart illustrating an exemplary process for producing an orthodontic appliance (referred to herein as "top aligner") for adjustment of the teeth and bone of the upper jaw of a human patient in accordance with the present disclosure.
Figure 2B:
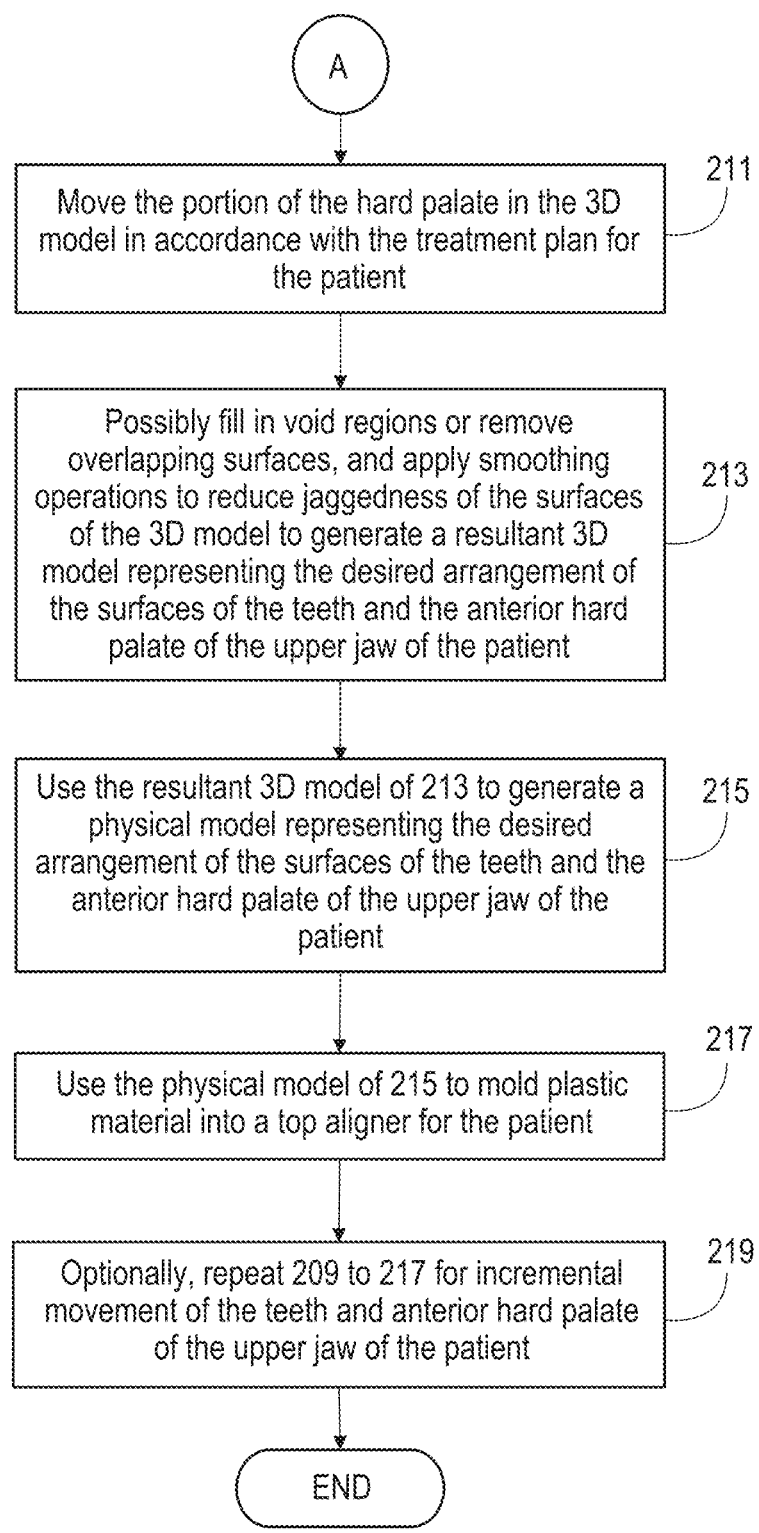

FIGS. 2A and 2B illustrates a process 200 for producing an orthodontic appliance (referred to herein as "top aligner") for adjustment of the teeth and bone of the upper jaw of a human patient. The top aligner is specific to the patient and placed in the patient's mouth during use.

Figure 3:
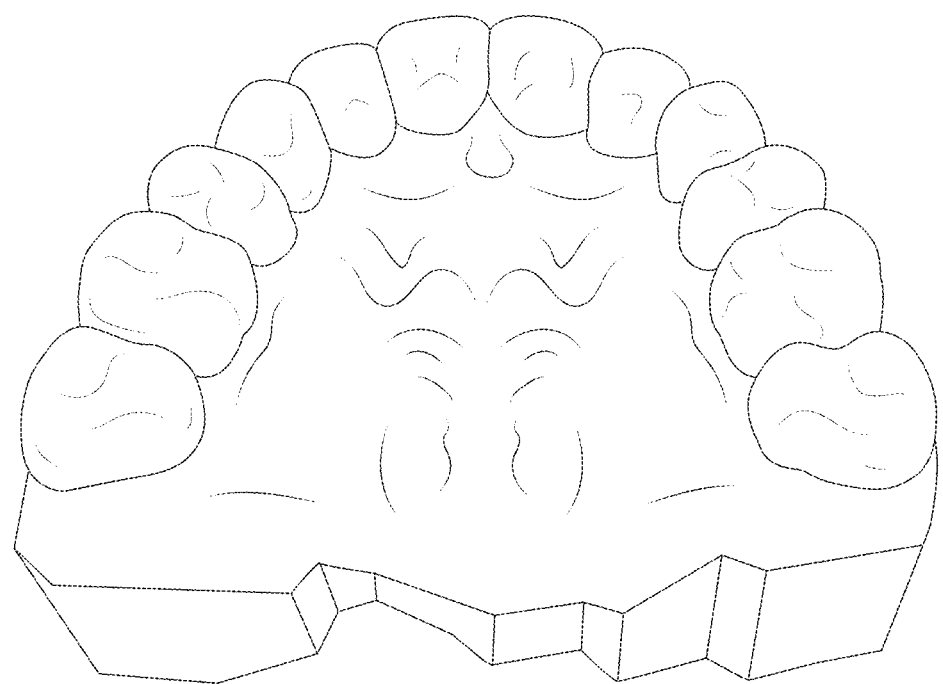
FIG. 3 is an image that depicts an exemplary cast of the teeth and the anterior hard palate of the upper jaw of a patient in accordance with the present disclosure.

In block 201, a cast (or plaster model) can be made of the teeth and the anterior hard palate of the upper jaw of the patient. The cast can be made from an impression of the teeth and the anterior hard palate of the upper jaw of the patient. The cast can be obtained by well-known techniques, such as those described in Graber, Orthodontics: Principle and Practice, Second Edition, Saunders, Philadelphia, 1969, pp. 401-415. FIG. 3 shows an example cast of the teeth and the anterior hard palate of the upper jaw of a patient. Alternatively, a three-dimensional (3D) scan can be taken of the teeth and the anterior hard palate of the upper jaw of the patient. For example, the teeth and the anterior hard palate of the upper jaw of the patient can be scanned or imaged using X-rays, three dimensional X-rays, computer-aided tomographic images or data sets, or magnetic resonance images, among others. In one example, a 3D scanner sold commercially under the brand TRIOS INTRAORAL SCANNER by 3Shape of Copenhagen, Denmark, can be used to take a three-dimensional scan can be taken of the teeth and the anterior hard palate of the upper jaw of the patient. Such scanning operations can avoid taking an impression of the teeth and the anterior hard palate of the upper jaw of the patient and making the cast therefrom.

In block 203, the cast of 201 can used to construct a 3D model of the exposed surfaces of the teeth and the anterior hard palate of the upper jaw of the patient. For example, a laser 3D scanner or contact 3D scanner can be operated to take a 3D scan of the cast of 201, and such 3D scan results can be used to construct a 3D model of the exposed surfaces of the teeth and the anterior hard palate of the upper jaw of the patient using well-known 3D modeling techniques. The 3D model can represent the surface topology of the teeth and hard palate of the upper jaw of the patient as a set of polygons of appropriate sizes and shapes joined at their edges. The set of polygons defining the 3D object is referred to as the "model" or "surface mesh" or "mesh". In one embodiment, the polygons can be triangles. In this embodiment, a triangle mesh is a piecewise linear surface with triangular faces joined along their edges.

Figure 4:
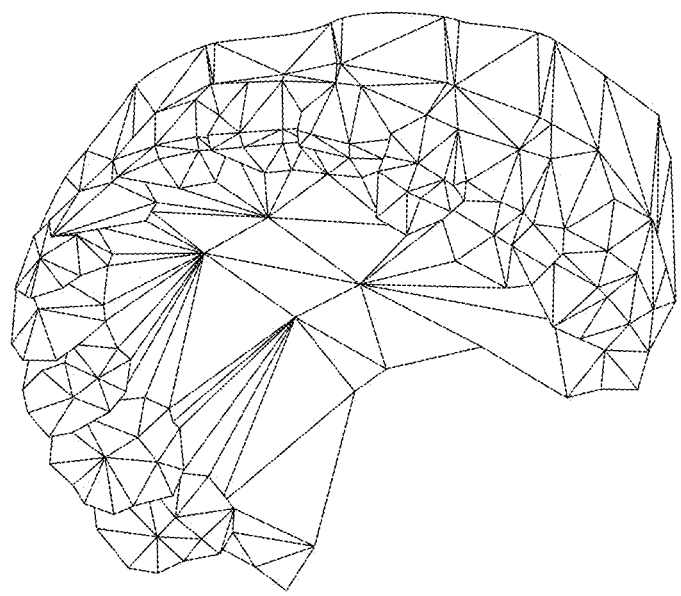
FIG. 4 is a schematic diagram illustrating an example 3D model of the surfaces of the teeth and the anterior hard palate of the upper jaw of a patient in accordance with the present disclosure.

Alternatively, in block 203, 3D scan results of 201 can used to construct a 3D model of the exposed surfaces of the teeth and the anterior hard palate of the upper jaw of the patient using well-known 3D modeling techniques. For example, many types of 3D scanners can be configured to provide a 3D model (e.g., a triangular surface mesh) of the teeth and hard palate of the upper jaw. Other 3D scanners provide data in the form of volume elements ("voxels") that can be converted into a digital model of the tooth and palate surfaces of the upper jaw. In one implementation, a marching cubes algorithm can be used to convert the voxels into a mesh. A smoothing operation can be applied to the mesh to reduce the jaggedness on the surfaces of the mesh caused by the marching cubes conversion. FIG. 4 depicts an example 3D model of the surfaces of the teeth and the anterior hard palate of the upper jaw of a patient.

In block 205, the 3D model of 203 is processed to segment or isolate surfaces for each tooth of the upper jaw in the 3D model. The isolated surfaces corresponding to an individual tooth are referred to an "isolated tooth" herein, and the isolated surfaces corresponding to the collective teeth of the upper jaw are referred to as "isolated teeth" herein. Such tooth segmentation can be performed manually based on user input, automatically by software-based operations without user input, or semi-automatically involving a combination of software-based operations with user input. Examples of operations for tooth segmentation are described in US Patent Publ. No. 2004/0096799 to Hughes at al., herein incorporated by reference in its entirety.

In block 207, the 3D model of 203 is processed to segment or isolate surfaces corresponding to all or part of the hard palate of the upper jaw in the 3D model. These surfaces are referred to an "isolated palate portion" herein. Similar to the tooth segmentation of 205, the palate segmentation can be performed manually based on user input, automatically by software-based operations without user input, or semi-automatically involving a combination of software-based operations with user input.

Figure 17:
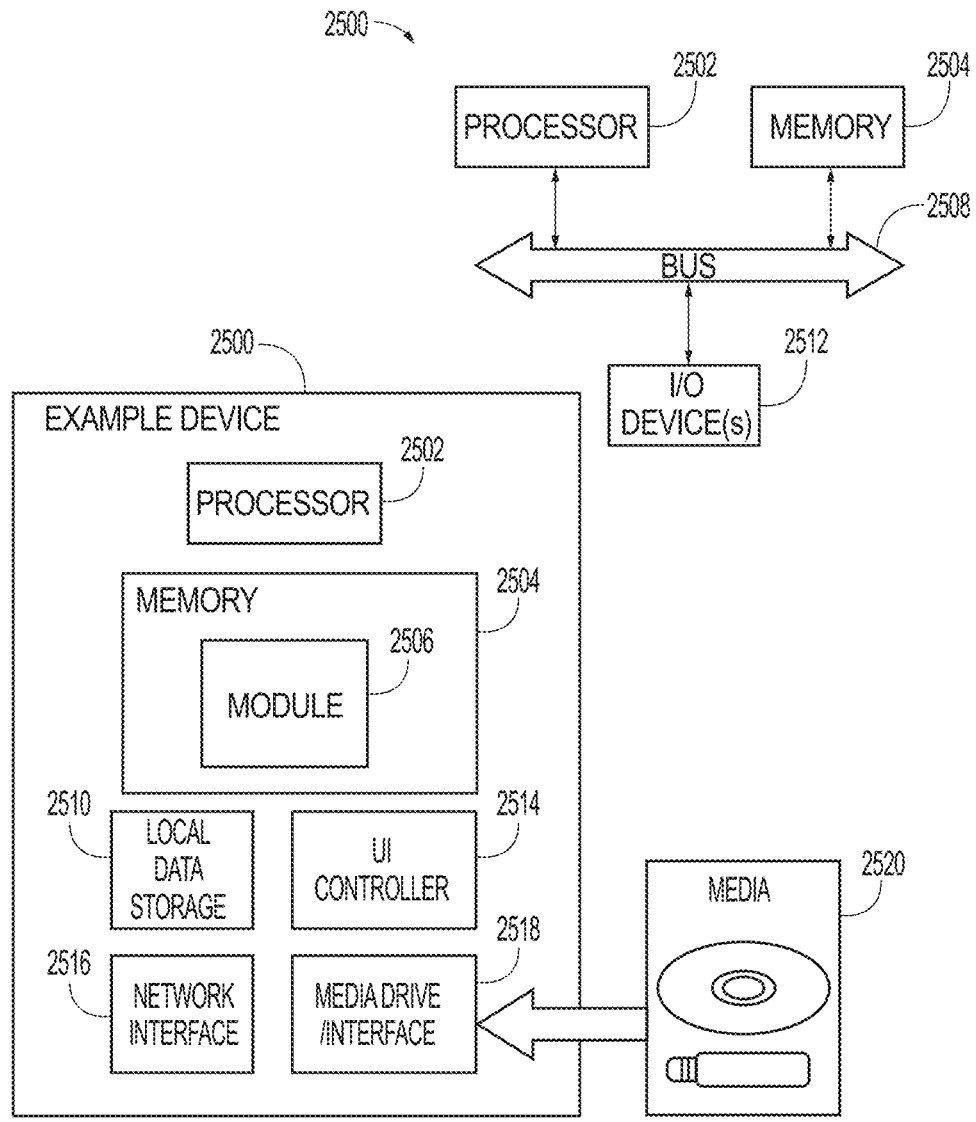
FIG. 17 is a schematic diagram of an exemplary computer processing system.

In block 209, at least one isolated tooth can be moved in the 3D model in accordance with a treatment plan for the patient. The tooth movement in the 3D model can be performed manually based on user input, automatically by software-based operations without user input, or semi-automatically involving a combination of software-based operations with user input. In one example, such tooth movement can be based on software-based rules and algorithms performed on a computer (FIG. 17). In embodiments, such rules and algorithms can be derived by modeling and simulating interaction and possible occlusion of the teeth of the upper and lower jaws of the patient, an attraction model between selected points on adjacent teeth, and/or an optimization function or process that optimizes placement of the teeth relative to an ideal form. In embodiments, the tooth movement can be based on measurement of maxillary position according to the technique of Prof. John Mew, which involves a linear measurement from the biting edge of the front teeth of the upper jaw to the tip of the nose and comparison of the measurement to an ideal value adjusted by age of the patient. The measurement can be used to determine if the upper jaw is retruded (and quantify the level of retrusion), protruded (and quantify the level of protrusion), or in normal position. See *Mew Indicator Line: Maxilla Positioning by Prof. John Mew—Mewingpedia*. In the event that the upper jaw is retruded, the tooth position can be set to expand the teeth of the upper jaw in the 3D model to correct for the retrusion of the upper jaw. In the event that the upper jaw is protruded, the tooth position can be set to retract the teeth of the upper jaw in the 3D model to correct for the protrusion of the upper jaw.

In block 211, the isolated palate portion can be moved in the 3D model in accordance with a treatment plan for the patient. The movement of palate portion in the 3D model can be performed manually based on user input, automatically by software-based operations without user input, or semi-automatically involving a combination of software-based operations with user input. In one example, the movement of the palate portion in the 3D model can be based on software-based rules and algorithms performed on a computer (FIG. 17). In embodiments, such rules and algorithms can be derived by modeling and simulating interaction and possible occlusion of the teeth of the upper and lower jaws of the patient, an attraction model between selected points on adjacent teeth, and/or an optimization function or process that optimizes placement of the teeth relative to an ideal form. In embodiments, the movement of the palate portion can be based on measurement of maxillary position according to the technique of Prof. John Mew as described herein. In the event that the upper jaw is retruded, the palate position can be set to move the palate portion forward and upward in the 3D model to correct for the retrusion of the upper jaw. In the event that the upper jaw is protruded, the palate position can be set to move the palate portion rearward and downward in the 3D model to correct for the protrusion of the upper jaw.

In block 213, the 3D model that results from the processing of 209 and 211 can be processed to fill in void regions or remove overlapping surfaces (if any exist) and to apply smooth operations to reduce jaggedness of the 3D model. As part of 213 (or 203), a decimation operation can optionally be applied to the 3D model to smooth the 3D model (e.g., mesh) and eliminate data points, which improves processing speed. The 3D model can also be simplified by removing unwanted or unnecessary sections of the model to increase data processing speed and enhance visual display. Unnecessary sections include those not needed for creation of the top aligner. The removal of these unwanted sections reduces the complexity and size of the 3D model, thus accelerating manipulations of the 3D model and other operations. Once the 3D model has been processed to provide a desired arrangement of the teeth and hard palate of the upper jaw of the patient, the resultant 3D model is generated and stored. This resultant 3D model represents the desired geometry of the surfaces of the teeth and the anterior hard palate of the upper jaw of the patient.

In blocks 215 and 217, the resultant 3D model of 213 is used to create the top aligner. More specifically, in block 215, the resultant 3D model of 213 is used to generate a physical model (three-dimensional physical structure) representing the desired geometry of the surfaces of the teeth and the anterior hard palate of the upper jaw of the patient. For example, a rapid prototyping device, such as a stereolithography machine, selectively hardens a liquid or other non-hardened resin into the physical model. Suitable rapid prototyping machines are commercially available from 3D Systems of Valencia, Calif.

In block 217, the physical model of 215 can be used as a mold (e.g., positive mold) to fabricate the top aligner. A conventional pressure or vacuum molding machine can be used to produce the top aligner from a suitable thermoformable material, such as thermal forming dental material available from Tru-Tain Incorporated of Rochester, Minn. or the Zendura™ thermal forming dental material available from Bay Materials LLC of Fremont, Calif. Suitable pressure molding equipment is available under the trade name BIOSTAR from Great Lakes Orthodontics, Ltd. of Tonawanda, N.Y. The top aligner includes a clear transparent polymeric shell configured with a tooth-receiving cavity whose geometry corresponds to the desired geometry of the surfaces of the teeth of the patient intended for the top aligner. The top aligner also includes a polymeric segment that is integral to the shell. The segment covers the anterior hard palate of the upper jaw of the patient intended for the top aligner. The shell can be configured to fit over the teeth of the upper jaw of the patient during use. The geometry and material properties of the shell can be configured to apply corrective forces to one or more teeth of the upper jaw of the patient during use. The palate segment (or portion thereof) can possibly contact the anterior hard palate of the upper jaw of the patient during use. The geometry and material properties of the palate segment (or portion thereof) can be configured to apply corrective forces to the anterior hard palate of the upper jaw of the patient during use. In some embodiments, the polymeric shell can apply corrective forces to all of the teeth of the upper jaw of the patient. In other embodiments, the polymeric shell can apply corrective forces to only certain one(s) of the teeth of the upper jaw, while others of the teeth will provide a base or an anchor region for holding the top aligner in place. In some embodiments, the polymeric shell can apply corrective forces to the anterior hard palate of the upper jaw of the patient. In other embodiments, the polymeric shell need not apply corrective forces to the anterior hard palate of the upper jaw of the patient.

In embodiments, for example where the upper jaw is retruded, the top aligner can be configured such that it applies corrective forces that expand the teeth of the upper jaw and move the anterior hard palate of the user forward and upward when worn by the patient. Such corrective forces are intended to correct for the retrusion of the upper jaw. In this embodiment, the palate segment (or portion thereof) of the top aligner can be in a state of compression when the top aligner is worn by the patient such that the resilient material properties of the palate segment (or portion thereof) contributes to the corrective forces that expand the teeth of the upper jaw and move the anterior hard palate of the patient forward and upward.

In other embodiments, for example where the upper jaw is protruded, the top aligner can be configured such that it applies corrective forces that retracts the teeth of the upper jaw and permits the anterior hard palate of the patient to move rearward and downward when worn by the patient. Such corrective forces are intended to correct for the protrusion of the upper jaw. In this embodiment, the palate segment of the top aligner can be in a state of tension when the top aligner is worn by the patient such that the resilient material properties of the palate segment (or portion thereof) contributes to the corrective forces that retracts the teeth of the upper jaw.

In embodiments, the top aligner can omit any wires or other means for holding the top aligner in place over the teeth or for applying corrective forces to the teeth and anterior hard palate of the upper jaw. In other embodiments, wires or other devices can be affixed to the shell of the top aligner to achieve certain capabilities. For example, it may be desirable or necessary to provide individual anchors on one or more teeth of the upper jaw with corresponding receptacles or apertures in the polymeric shell of the top aligner so that the aligner can apply an upward force on the tooth that would not be possible in the absence of such an anchor.

In block 219, the operations of 209 to 217 can be repeated to produce a set of top aligners for incremental movement of the teeth and anterior hard palate of the upper jaw of the patient. The patient wears each top aligner of the set for a period of time that permits the corrective forces applied by the top aligner to move one or more teeth and possibly the hard palate of the upper jaw of the patient. At that point, the patient replaces the current top aligner with the next top aligner in the set until the desired correction has been achieved. Conveniently, the top aligners of the set are generally not affixed to the teeth and the patient may place and replace the top aligners at any time during treatment.

After production, the set of top aligners can be supplied to the treating clinician (or patient) all at one time. The set of top aligners can be marked in some manner, typically by sequential numbering directly on the top aligners or on tags, pouches, or other items which are affixed to or which enclose each top aligner, to indicate their order of use. Optionally, written instructions may accompany the set of top aligners which set forth that the patient is to wear the individual top aligners in the order marked on the aligners or elsewhere in the packaging. Use of the top aligners in such a manner can be configured to reposition the teeth and possibly the anterior hard palate of the upper jaw of the patient progressively toward a desired final arrangement. Because a patient's teeth may respond differently than originally expected, the treating clinician may wish to evaluate the patient's progress during the course of treatment. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few top aligners, delaying production on subsequent top aligners until the patient's progress has been evaluated.

In embodiments, the clinician and patient can employ a smartphone application (or web-based application) and related service to connect to one another for reviewing and revising the treatment plan for the patient that involves one or more top aligners as described herein. Exemplary functionality of the application and related service is described herein.

Figure 5:
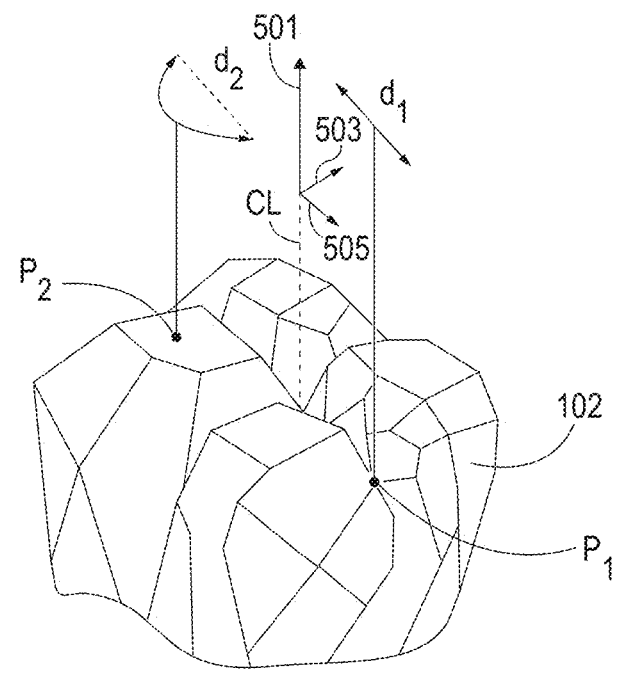
FIG. 5 is a schematic diagram illustrating movement of a tooth in a 3D model of the surfaces of the teeth and the anterior hard palate of the upper jaw of a patient in accordance with the present disclosure.

FIG. 5 illustrates movement of a tooth of the upper jaw in the 3D model of the teeth and anterior hard palate of the upper jaw (block 209). As a frame of reference describing how the tooth can be moved, an arbitrary centerline (CL) may extend through the tooth. A set of orthogonal directions represented by references axes 501, 503, 505 can be defined in reference to the centerline CL. The tooth can be moved in any one direction (or combination of directions) corresponding to the references axes 501, 503, 505. Furthermore, the tooth may be rotated such that the centerline CL rotates about the axis 505 or rotated about axis 503. Additionally, the tooth may be rotated such that the centerline CL rotates about the axis 501. Furthermore, combinations of directional movement and/or axial rotations of the tooth can be performed. Thus, all possible free-form motions of the tooth can be performed. FIG. 5 further illustrates how the magnitude of tooth movement can be defined in terms of a maximum linear translation of any arbitrary point P on a tooth. Each point P will undergo a cumulative translation as that tooth is moved in any of the orthogonal or rotational directions defined in FIG. 5. That is, while the point will usually follow a nonlinear path, there is a linear distance between any point in the tooth when determined at different times during the treatment. Thus, the arbitrary point P may in fact undergo a true side-to-side translation as indicated by arrow dl, while a second arbitration point P2 may travel along an arcuate path, resulting in a final translation d2.

Figure 6:
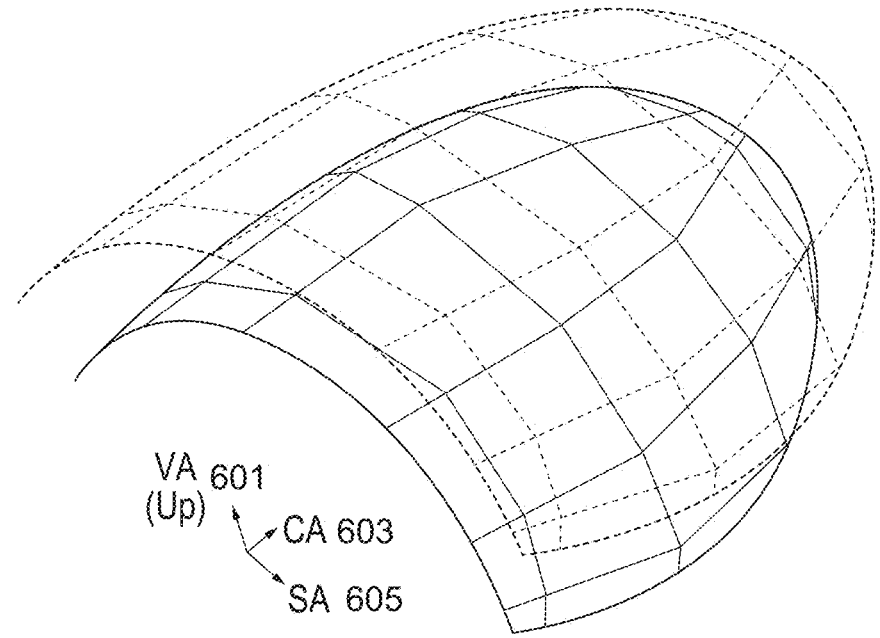
FIG. 6 is a schematic diagram illustrating movement of a palate segment (or section) in a 3D model of the surfaces of the teeth and the anterior hard palate of the upper jaw of a patient in accordance with the present disclosure.

FIG. 6 illustrates movement of the palate portion of the upper jaw in the 3D model of the teeth and anterior hard palate of the upper jaw (block 211). As a frame of reference describing how the palate portion can be moved, an arbitrary reference frame represented by references axes 601 (labeled "VA" for vertical or up axis, 603 (labeled "CA" for coronal axis), 605 (labeled "SA" for sagittal axis) can be defined at or near the rear of the anterior hard palate of the upper jaw. The palate portion can be moved in any one direction (or combination of directions) corresponding to the references axes 601, 603, 605. Furthermore, the palate portion of the tooth may be rotated about the axis 605 or rotated about axis 603. Additionally, the palate portion may be rotated about the axis 601. Furthermore, combinations of directional movement and/or axial rotations of the palate portion can be performed. Thus, all possible free-form motions of the palate portion can be performed. Alternatively, the palate portion can be moved or stretched or transformed in a more complex manner over directions and/or magnitudes that vary according to position or orientation in the 3D model.

In embodiments, the top aligner can be configured to move the teeth and/or palate portion of the upper jaw in a range of 0.1-0.3 mm. The typical movement can be 0.25 mm when the top aligner is worn for 2 weeks. However, the movement can be reduced to half or 0.125 mm and the top aligner is worn for 1 week. This creates a light, continuous force.

Furthermore, segments (or parts) of the teeth and/or palate portion of the upper jaw can be moved or stretched or transformed in a piecewise manner over varying directions and/or magnitudes over time if desired. For example, in one illustrative embodiment, the movement of the teeth of the upper jaw can be carried out in a sequence of three phases. In a first phase, the top aligner is configured to move the anterior teeth of the upper jaw (i.e., the incisors 1, 2 and canine 3 of FIG. 1) vertically upward to intrude the anterior teeth of the upper jaw. In a second phase that follows the first phase, another top aligner is configured to move the middle teeth of the upper jaw (i.e., the premolars 4,5 of FIG. 1) vertically upward to intrude the middle teeth of the upper jaw. In a third phase that follows the second phase, yet another top aligner is configured to move the back teeth of the upper jaw (i.e., the molars 6,7 of FIG. 1) vertically upward to intrude the back teeth of the upper jaw. In the third phase, the anterior teeth typically extrude back down to some degree due to the opposite force created by intruding the back teeth. This sequence of top aligners can be used to rotate that upper maxilla vertically upwards (in the VA (UP) direction) and forwards (in the CA direction).

In other embodiments, an impression can be taken of the tongue of the patient, and the profile (size and shape) of the tongue can be measured from the tongue impression. The target position of the teeth (arch) and the palate of the upper jaw at the end of the treatment plan for the patient can be selected to accommodate the measured profile (size and shape) of the tongue of the patient.

Figure 7:
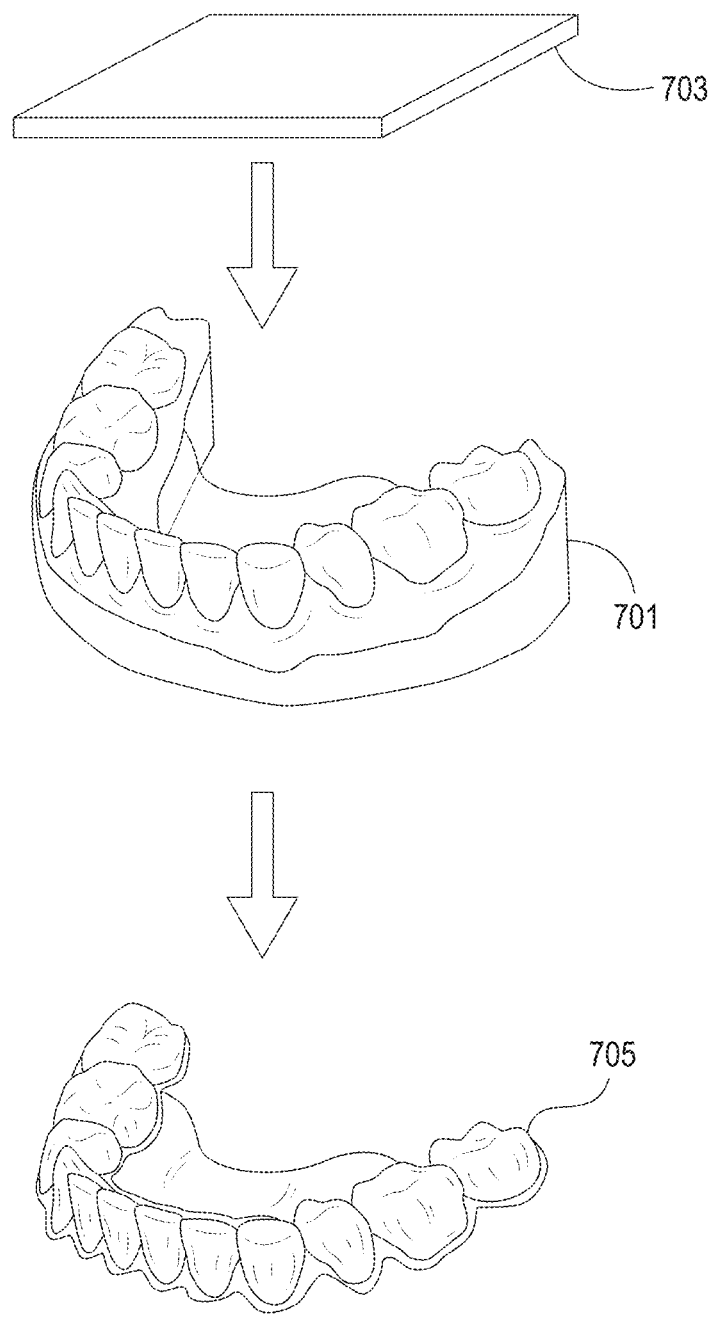
FIG. 7 is a schematic diagram illustrating operations that form a top aligner that covers the surfaces of the teeth and the anterior hard palate of the upper jaw of a patient in accordance with the present disclosure.
Figure 8A:
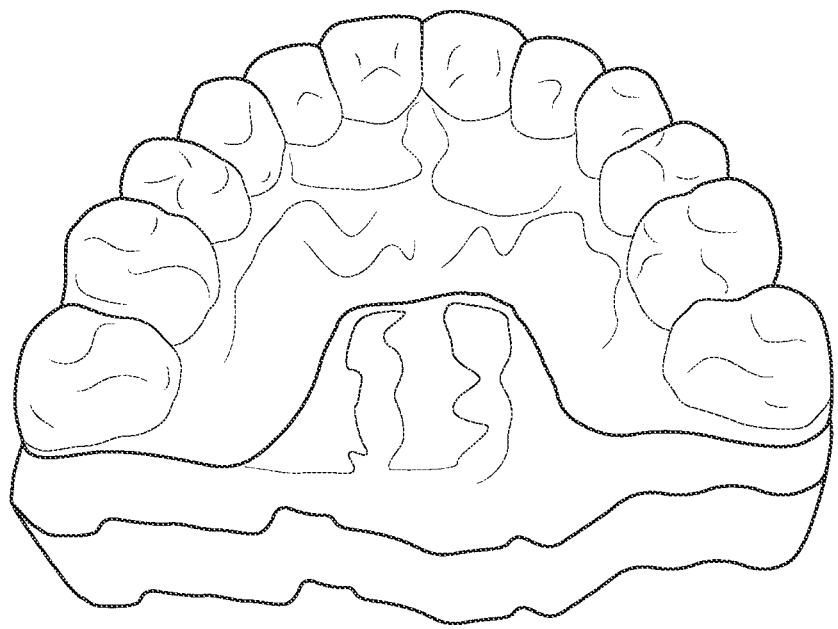
FIGS. 8A and 8B are schematic representations of exemplary top aligners in accordance with the present disclosure.
Figure 8B:
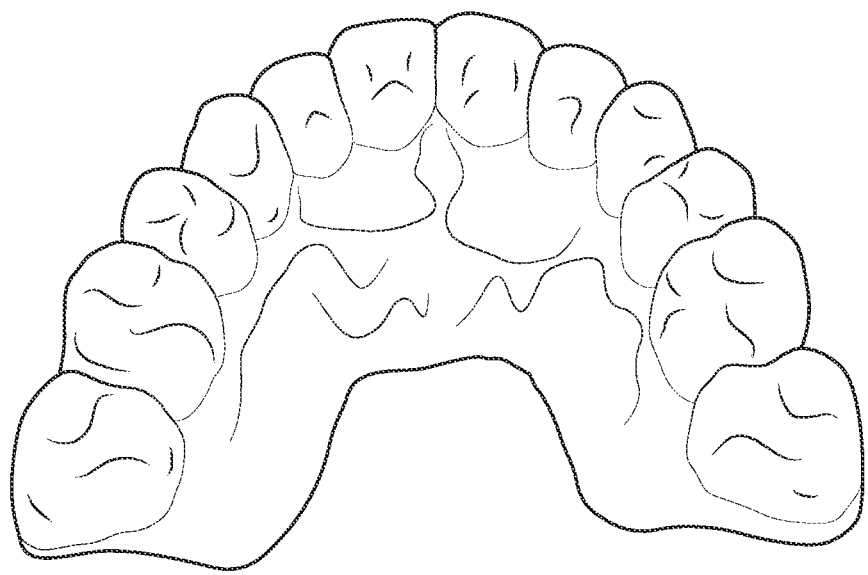

FIG. 7 illustrates the operations that create the top aligner (blocks 215 and 217) More specifically, the resultant 3D model (block 213) can be used to generate a physical model (three-dimensional physical structure) 701 representing the desired geometry of the surfaces of the teeth and the anterior hard palate of the upper jaw of the patient. And the physical model 701 can be used as a mold (e.g., positive mold) to mold a sheet of clear transparent polymeric material 703 into the top aligner 705. FIGS. 8A and 8B depict exemplary top aligners formed by such operations. In the embodiment of FIG. 8A, the top aligner is configured such that the top aligner does not cover all (the entirety) of the hard palate of the patient. Specifically, a part of the top aligner that covers that central rear portion of the hard palate of the patient can be trimmed or otherwise removed to provide a generally u-shaped contour that extends over the palate of the patient as shown. Such trimming can be used to alleviate patient discomfort or accommodate tori in the upper jaw of the patient. In the embodiment of FIG. 8B, the top aligner is configured such that the top aligner does cover all (the entirety) of the hard palate of the patient.

Figure 9:
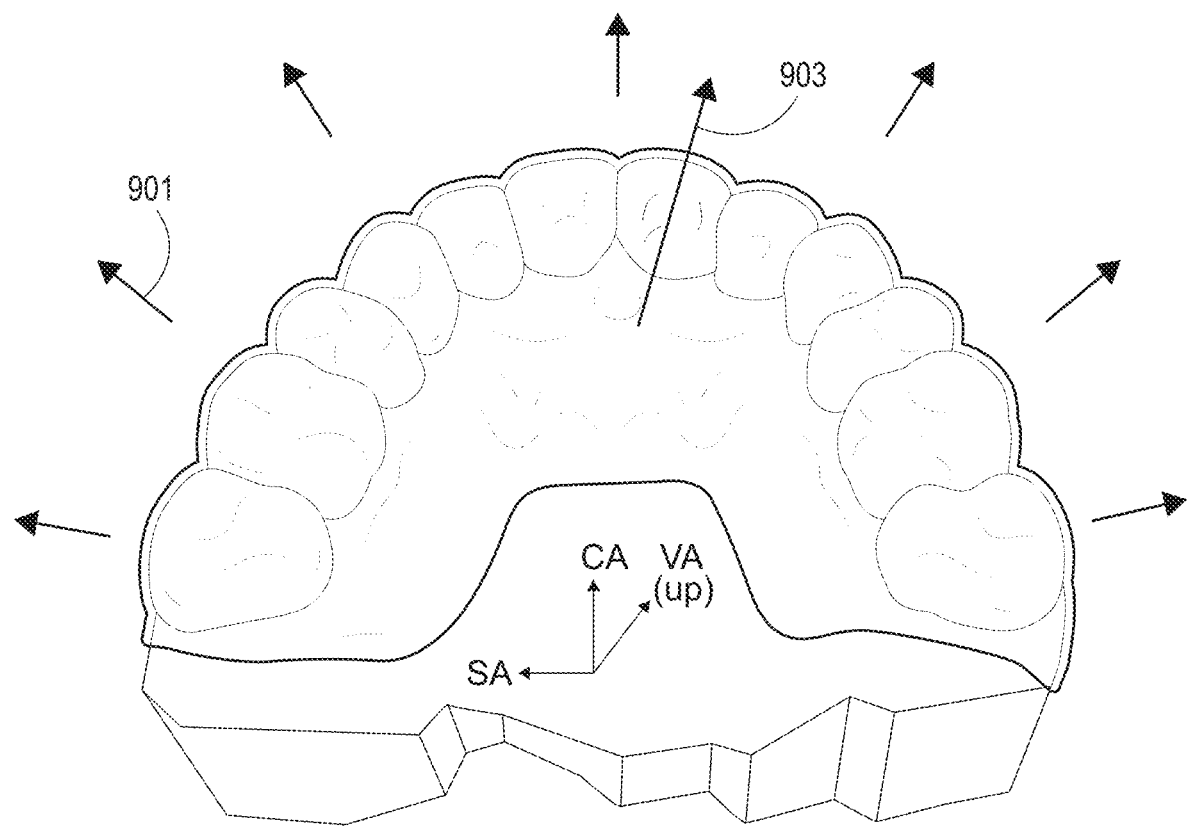
FIG. 9 is a schematic diagram illustrating exemplary corrective forces applied by a top aligner to the teeth and bone of the upper jaw of a patient in accordance with the present disclosure.

When worn by the user, the polymeric shell of the top aligner can apply corrective forces to all or only certain one(s) of the teeth of the upper jaw. The top aligner can also apply corrective forces to the anterior hard palate of the upper jaw. The corrective forces can move or rotate the teeth and/or the palate of the upper jaw in one or more desired directions or orientations as described herein. FIG. 9 illustrates an exemplary embodiment where the top aligner applies corrective forces that expand the upper jaw and move the teeth of the upper jaw outward as indicated by arrows 901. In this configuration, the corrective forces expand the molars in the UL quadrant of the upper jaw (one shown corresponding to tooth 6 of the UL quadrant in FIG. 1) with a component in the outward direction (i.e., the SA direction toward the right side of the page) and possibly a component in the upward direction (i.e., the VA (UP) direction into the page). The corrective forces can also expand the molars in the UR quadrant of the upper jaw (one shown corresponding to tooth 6 of the UR quadrant in FIG. 1) with a component in the outward direction (i.e., the SA direction toward the left side of the page) and possibly a component in the upward direction (i.e., the VA (UP) direction into the page). The corrective forces can also expand the premolars and canine and lateral incisor in the UL quadrant of the upper jaw (four shown corresponding to teeth 5 to 2 in the UL quadrant in FIG. 1) with a component in the outward direction (i.e., the SA direction toward the right side of the page) and a component in the forward direction (i.e., the CA direction toward the top of the page) and possibly a component in the upward direction (i.e., the VA (UP) direction into the page). The corrective forces can also expand the premolars and canine and lateral incisor in the UR quadrant of the upper jaw (four shown corresponding to teeth 5 to 2 in the UR quadrant in FIG. 1) with a component in the outward direction (i.e., the SA direction toward the left side of the page) and a component in the forward direction (i.e., the CA direction toward the top of the page) and possibly a component in the upward direction (i.e., the VA (UP) direction into the page). The corrective forces can also expand the central incisors in the UL and UR quadrants of the upper jaw (two shown corresponding to tooth 1 in the UL and UR quadrants in FIG. 1) with a component in the forward direction (i.e., the CA direction toward the top of the page) and possibly a component in the upward direction (i.e., the VA (UP) direction into the page). The top aligner can also apply corrective forces that moves the anterior hard palate of the upper jaw upward and forward (i.e., with components in the VA (UP) and CA directions) as indicated by arrow 903. Such corrective forces can be used to correct for retrusion of the upper jaw as described herein. For a narrow palate, the top aligner can also be configured to apply corrective forces that expands and moves the hard palate in sagittal plane of the patient.

Figure 10A:
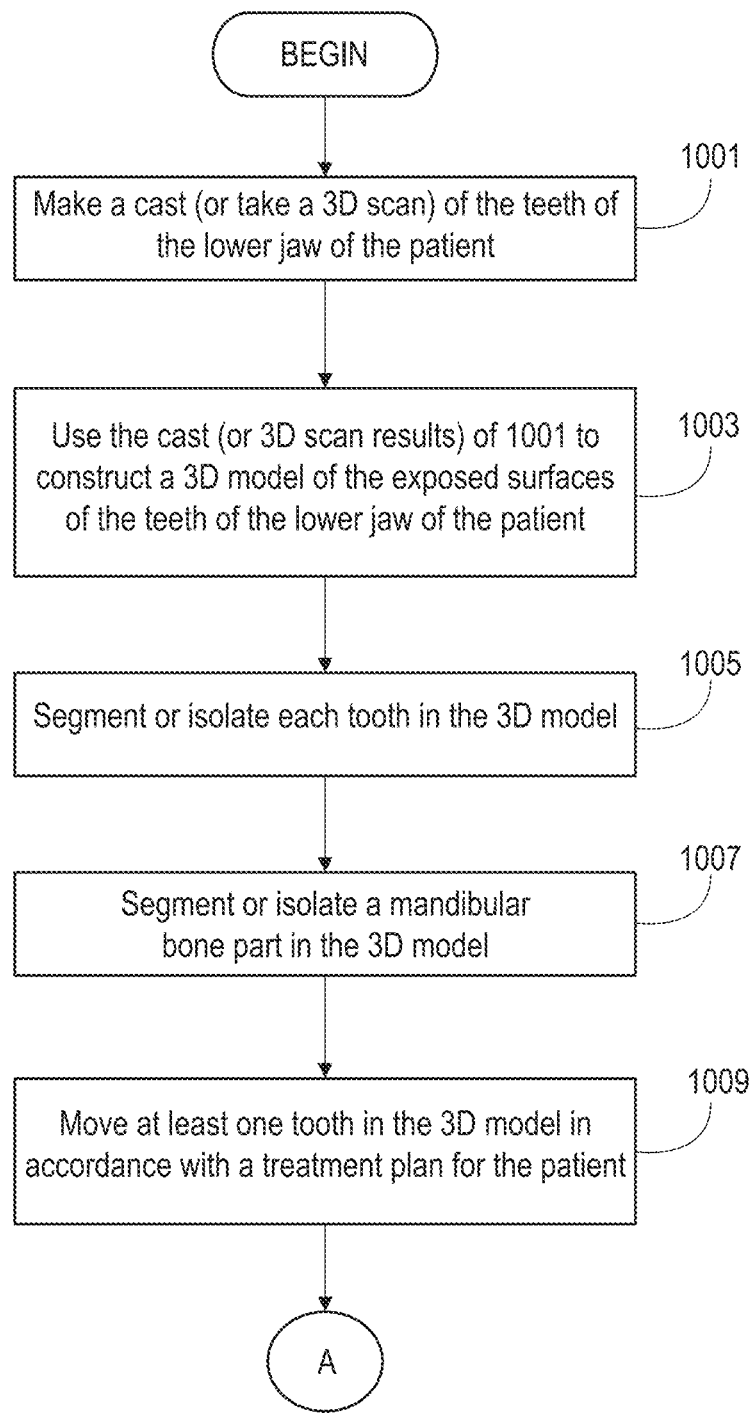
FIGS. 10A to 10B, collectively, is a flow chart illustrating an exemplary process for producing an orthodontic appliance (referred to herein as "bottom aligner") for adjustment of the teeth and bone of the lower jaw of a human patient in accordance with the present disclosure.
Figure 10B:
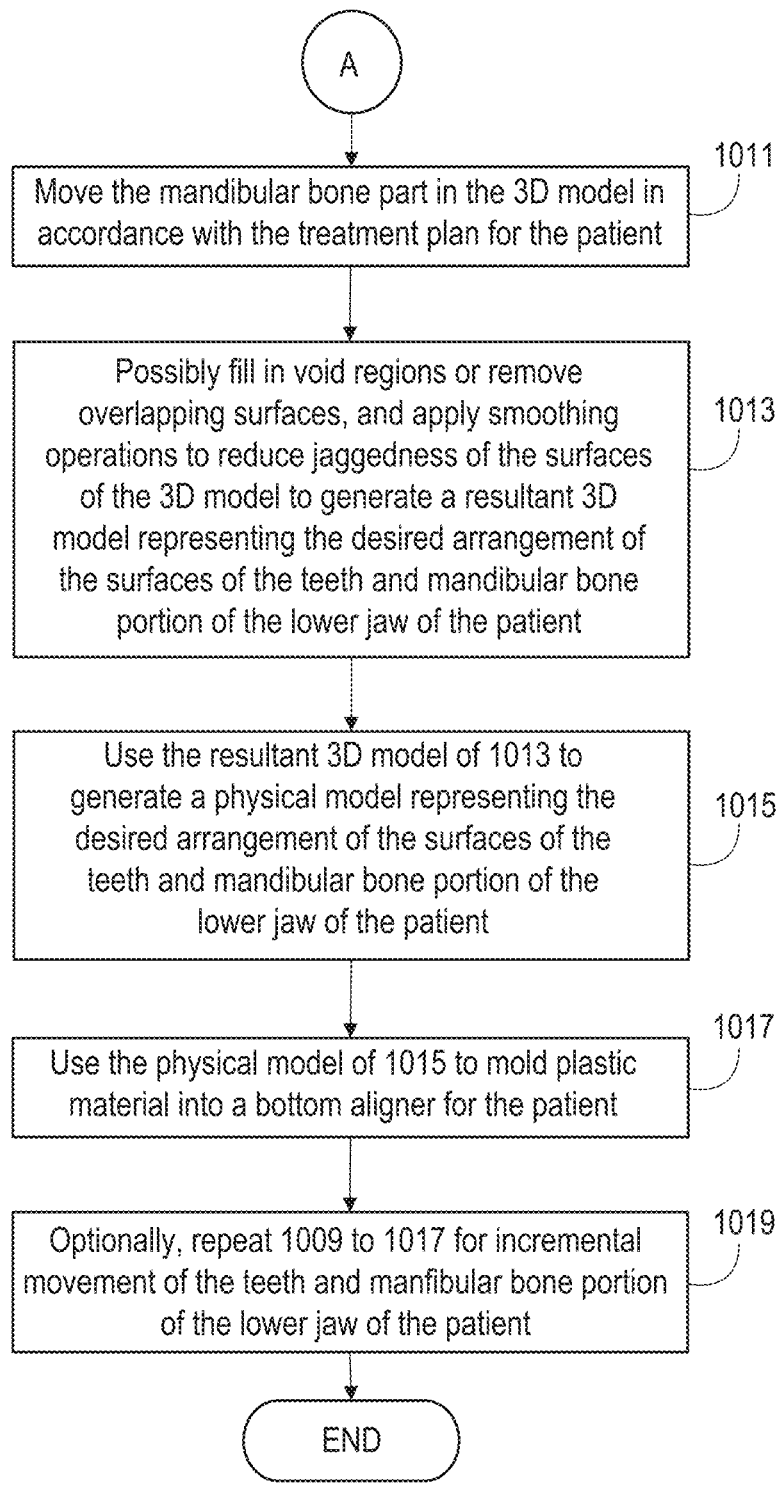

FIGS. 10A and 10B illustrate a process 1000 for producing an orthodontic appliance (referred to herein as "bottom aligner") for adjustment of the teeth of the lower jaw of a human patient. The bottom aligner is specific to the patient and placed in the patient's mouth during use.

Figure 11:
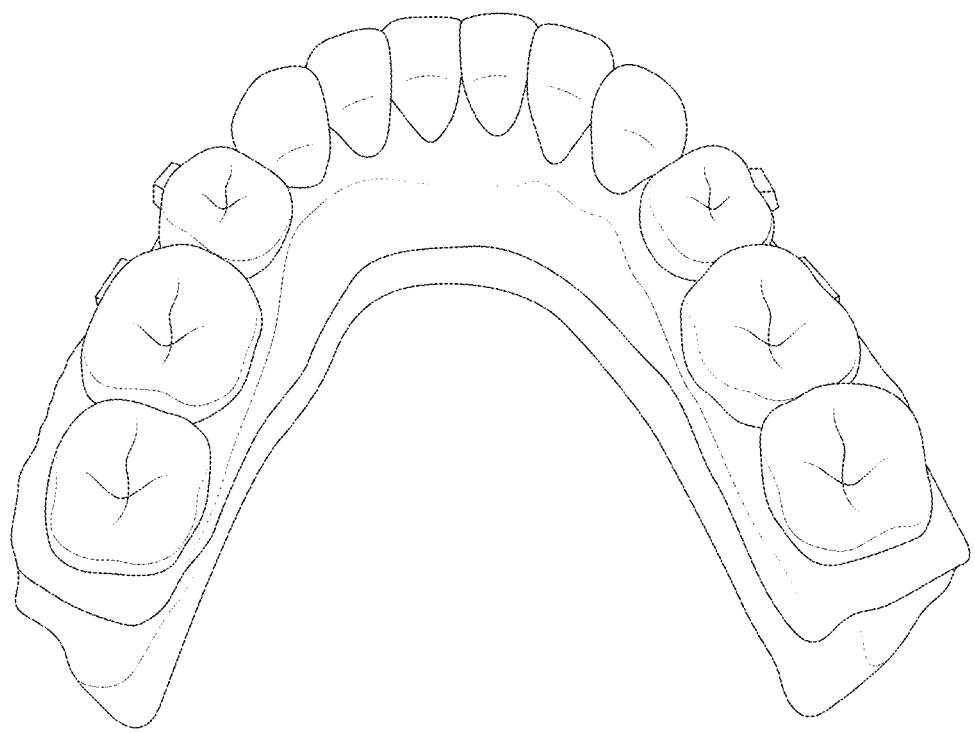
FIG. 11 is an image that depicts an exemplary cast of the teeth and mandibular bone portion of the lower jaw of a patient in accordance with the present disclosure.

In block 1001, a cast (or plaster model) can be made of the teeth of the lower jaw and the mandibular bone below the gingiva of the lower jaw of the patient. The cast can be made from an impression of the teeth of the lower jaw and the mandibular bone below the gingiva of the lower jaw of the patient. The cast can be obtained by well-known techniques, such as those described in Graber, Orthodontics: Principle and Practice, Second Edition, Saunders, Philadelphia, 1969, pp. 401-415. FIG. 11 shows an example cast of the teeth of the lower jaw and the mandibular bone below the gingiva of the lower jaw of the patient. Alternatively, a three-dimensional (3D) scan can be taken of the teeth of the lower jaw and the mandibular bone below the gingiva of the lower jaw of the patient. For example, the teeth and the mandibular bone of the lower jaw of the patient can be scanned or imaged using X-rays, three dimensional X-rays, computer-aided tomographic images or data sets, or magnetic resonance images, among others. In one example, a 3D scanner sold commercially under the brand TRIOS INTRAORAL SCANNER by 3Shape of Copenhagen, Denmark, can be used to take a three-dimensional scan can be taken of the teeth and the mandibular bone of the lower jaw of the patient. Such scanning operations can avoid taking an impression of the teeth and the mandibular bone of the lower jaw of the patient and making the cast therefrom.

In block 1003, the cast of 1001 can used to construct a 3D model of the exposed surfaces of the teeth of the lower jaw and the surfaces of mandibular bone below the gingiva of the lower jaw of the patient. For example, a laser 3D scanner or contact 3D scanner can be operated to take a 3D scan of the cast of 1001, and such 3D scan results can be used to construct a 3D model of the exposed surfaces of the teeth and the surfaces of mandibular bone below the gingiva of the lower jaw of the patient using well-known 3D modeling techniques. The 3D model can represent the surface topology of the teeth of the lower jaw and the surface topology of the mandibular bone below the gingiva of the lower jaw of the patient as a set of polygons of appropriate sizes and shapes joined at their edges. The set of polygons defining the 3D object is referred to as the "model" or "surface mesh" or "mesh". In one embodiment, the polygons can be triangles. In this embodiment, a triangle mesh is a piecewise linear surface with triangular faces joined along their edges.

Figure 12:
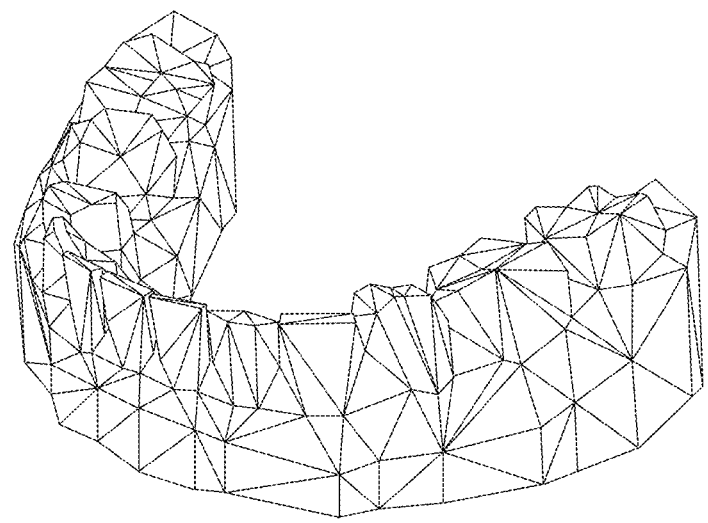
FIG. 12 is a schematic diagram illustrating an example 3D model of the surfaces of the teeth and mandibular bone portion of the lower jaw of a patient in accordance with the present disclosure.

Alternatively, in block 1003, the 3D scan results of 1001 can used to construct a 3D model of the exposed surfaces of the teeth of the lower jaw and the surfaces of mandibular bone below the gingiva of the lower jaw of the patient using well-known 3D modeling techniques. For example, many types of 3D scanners can be configured to provide a 3D model (e.g., a triangular surface mesh) of the teeth of the lower jaw. Other 3D scanners provide data in the form of volume elements ("voxels") that can be converted into a digital model of the tooth surfaces of the lower jaw. In one implementation, a marching cubes algorithm can be used to convert the voxels into a mesh. A smoothing operation can be applied to the mesh to reduce the jaggedness on the surfaces of the mesh caused by the marching cubes conversion. FIG. 12 depicts an example 3D model of the surfaces of the teeth and the surfaces of mandibular bone below the gingiva of the lower jaw of the patient.

In block 1005, the 3D model of 1003 is processed to segment or isolate each tooth of the lower jaw in the 3D model. The isolated surfaces corresponding to an individual tooth are referred to an "isolated tooth" herein, and the isolated surfaces corresponding to the collective teeth of the upper jaw are referred to as "isolated teeth" herein. Such tooth segmentation can be performed manually based on user input, automatically by software-based operations without user input, or semi-automatically involving a combination of software-based operations with user input. Examples of operations for tooth segmentation are described in US Patent Publ. No. 2004/0096799 to Hughes at al., herein incorporated by reference in its entirety.

In block 1007, the 3D model of 1003 is processed to segment or isolate surfaces corresponding to a portion of the mandibular bone below the gingiva of the lower jaw in the 3D model. These surfaces are referred to an "isolated mandibular bone part" herein. Similar to the tooth segmentation of 1005, the mandibular bone segmentation can be performed manually based on user input, automatically by software-based operations without user input, or semi-automatically involving a combination of software-based operations with user input.

In block 1009, one or more of the isolated teeth can be moved in the 3D model in accordance with a treatment plan for the patient. The tooth movement in the 3D model can be performed manually based on user input, automatically by software-based operations without user input, or semi-automatically involving a combination of software-based operations with user input. In one example, such tooth movement can be based on software-based rules and algorithms performed on a computer (FIG. 17). In embodiments, such rules and algorithms can be derived by modeling and simulating interaction and possible occlusion of the teeth of the upper and lower jaws of the patient, an attraction model between selected points on adjacent teeth, and/or an optimization function or process that optimizes placement of the teeth relative to an ideal form. In embodiments, the tooth movement can be based on measurement of maxillary position according to the technique of Prof. John Mew as described herein. The measurement can be used to determine if the upper jaw is retruded (and quantify the level of retrusion), protruded (and quantify the level of protrusion), or in normal position. See *Mew Indicator Line: Maxilla Positioning by Prof. John Mew—Mewingpedia*. In the event that the upper jaw and lower jaw are retruded, the tooth position can be set to expand the teeth of the lower jaw in the 3D model to correct for the retrusion of the lower jaw. In the event that the upper jaw and lower jaw are protruded, the tooth position can be set to retract the teeth of the lower jaw in the 3D model to correct for the protrusion of the lower jaw.

In block 1011, the isolated mandibular bone part can be moved in the 3D model in accordance with a treatment plan for the patient. The movement of the mandibular bone part in the 3D model can be performed manually based on user input, automatically by software-based operations without user input, or semi-automatically involving a combination of software-based operations with user input. In one example, the movement of the mandibular bone part in the 3D model can be based on software-based rules and algorithms performed on a computer (FIG. 17). In embodiments, such rules and algorithms can be derived by modeling and simulating interaction and possible occlusion of the teeth of the upper and lower jaws of the patient, an attraction model between selected points on adjacent teeth, and/or an optimization function or process that optimizes placement of the teeth relative to an ideal form. In embodiments, the movement of the mandibular bone part can be based on measurement of maxillary position according to the technique of Prof. John Mew as described herein. In the event that the lower jaw is retruded, the position of the mandibular bone part can be set to move and expand the mandibular bone part in the sagittal plane of the patient to correct for the retrusion of the lower jaw. In the event that the lower jaw is protruded, the position of the mandibular bone part can be set to move and retract the mandibular bone part in the sagittal plane of the patient to correct for the protrusion of the lower jaw.

In block 1013, the 3D model that results from the processing of 1009 and 1011 can be processed to fill in void regions or remove overlapping surfaces (if any exist) and to apply smooth operations to reduce jaggedness of the 3D model. As part of 1013 (or 1003), a decimation operation can optionally be applied to the 3D model to smooth the 3D model (e.g., mesh) and eliminate data points, which improves processing speed. The 3D model can also be simplified by removing unwanted or unnecessary sections of the model to increase data processing speed and enhance visual display. Unnecessary sections include those not needed for creation of the top aligner. The removal of these unwanted sections reduces the complexity and size of the 3D model, thus accelerating manipulations of the 3D model and other operations. Once the 3D model has been processed to provide a desired arrangement of the teeth and mandibular bone portion of the lower jaw of the patient, the resultant 3D model is generated and stored. This resultant 3D model represents the desired geometry of the surfaces of the teeth and the mandibular bone portion of the lower jaw of the patient.

In blocks 1015 and 1017, the resultant 3D model of 1013 is used to create the lower aligner. More specifically, in block 1015, the resultant 3D model of 1013 is used to generate a physical model (three-dimensional physical structure) representing the desired geometry of the surfaces of the teeth and mandibular bone portion of the lower jaw of the patient. For example, a rapid prototyping device, such as a stereolithography machine, selectively hardens a liquid or other non-hardened resin into the physical model. Suitable rapid prototyping machines are commercially available from 3D Systems of Valencia, Calif.

In block 1017, the physical model of 1015 can be used as a mold (e.g., positive mold) to fabricate the bottom aligner. A conventional pressure or vacuum molding machine can be used to produce the bottom aligner from a suitable thermoformable material, such as thermal forming dental material available from Tru-Tain Incorporated of Rochester, Minn., or the Zendura™ thermal forming dental material available from Bay Materials LLC of Fremont, Calif. Suitable pressure molding equipment is available under the trade name BIOSTAR from Great Lakes Orthodontics, Ltd. of Tonawanda, N.Y. The bottom aligner includes a clear transparent polymeric shell configured with a tooth-receiving cavity whose geometry corresponds to the desired geometry of the surfaces of the teeth of the lower jaw of the patient intended for the bottom aligner. The polymeric shell can fit over the teeth of the lower jaw and contact the mandibular bone portion of the lower jaw of the patient. The geometry and material properties of the polymeric shell can be configured such that the shell applies corrective forces to one or more teeth of the lower jaw of the patient. The bottom aligner can also include a polymeric segment that is integral to the shell and configured to contact the mandibular bone portion of the lower jaw. The geometry and material properties of the polymeric segment that contacts the mandibular bone portion can be configured to apply corrective forces to the mandibular bone portion of the patient during use. In some embodiments, the polymeric shell can apply corrective forces to all of the teeth of the lower jaw of the patient. In other embodiments, the polymeric shell can apply corrective forces to only certain one(s) of the teeth of the lower jaw, while others of the teeth will provide a base or an anchor region for holding the bottom aligner in place. In some embodiments, the bottom aligner can apply corrective forces to the mandibular bone portion of the lower jaw of the patient. In other embodiments, the bottom aligner need not apply corrective forces to the mandibular bone portion of the lower jaw of the patient.

In embodiments, for example where the lower jaw is retruded, the geometry of the bottom aligner can be configured such that it applies corrective forces that expand the teeth and mandibular bone portion of the lower jaw when worn by the patient. Such corrective forces are intended to correct for the retrusion of the lower jaw. In this embodiment, a part (or all) of the bottom aligner can be in a state of compression when the bottom aligner is worn by the patient such that the resilient material properties of the bottom aligner contribute to the corrective forces that expand the teeth and mandibular bone portion of the lower jaw.

In other embodiments, for example where the lower jaw is protruded, the geometry of the bottom aligner can be configured such that it applies corrective forces that retracts the teeth and mandibular bone portion of the lower jaw when worn by the patient. Such corrective forces are intended to correct for the protrusion of the lower jaw. In this embodiment, a part (or all) of the bottom aligner can be in a state of tension when the bottom aligner is worn by the patient such that the resilient material properties of the bottom aligner contributes to the corrective forces that retracts the teeth and the mandibular bone portion of the lower jaw.

In embodiments, the bottom aligner can omit any wires or other means for holding the bottom aligner in place over the teeth or for applying corrective forces to the teeth and the mandibular bone portion of the lower jaw. In other embodiments, wires or other devices can be affixed to the shell of the bottom aligner to achieve certain capabilities. For example, it may be desirable or necessary to provide individual anchors on one or more teeth of the lower jaw with corresponding receptacles or apertures in the polymeric shell of the bottom aligner so that the aligner can apply corrective force on the tooth that would not be possible in the absence of such an anchor.

In block 1019, the operations of 1009 to 1017 can be repeated to produce a set of bottom aligners for incremental movement of the teeth and mandibular bone portion of the lower jaw of the patient. The patient wears each bottom aligner of the set for a period of time that permits the corrective forces applied by the bottom aligner to move one or more teeth and the mandibular bone portion (or part thereof) of the lower jaw of the patient. At that point, the patient replaces the current bottom aligner with the next bottom aligner in the set until the desired correction has been achieved. Conveniently, the bottom aligners of the set are generally not affixed to the teeth and the patient may place and replace the bottom aligners at any time during treatment.

After production, the set of bottom aligners can be supplied to the treating clinician (or patient) all at one time. The set of bottom aligners can be marked in some manner, typically by sequential numbering directly on the bottom aligners or on tags, pouches, or other items which are affixed to or which enclose each bottom aligner, to indicate their order of use. Optionally, written instructions may accompany the set of bottom aligners which set forth that the patient is to wear the individual bottom aligner in the order marked on the aligners or elsewhere in the packaging. Use of the bottom aligners in such a manner will reposition the teeth of the lower jaw of the patient progressively toward the desired final arrangement. Because a patient's teeth may respond differently than originally expected, the treating clinician may wish to evaluate the patient's progress during the course of treatment. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few bottom aligners, delaying production on subsequent bottom aligners until the patient's progress has been evaluated.

In embodiments, the clinician and patient can employ a smartphone application (or web-based application) and related service to connect to one another for reviewing and revising the treatment plan for the patient that involves one or more bottom aligners as described herein. Exemplary functionality of the application and related service is described herein.

Figure 13:
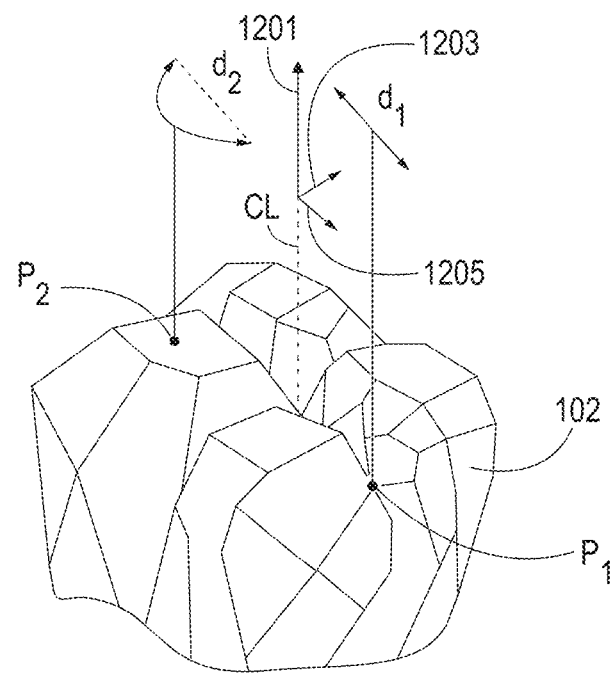
FIG. 13 is a schematic diagram illustrating movement of a tooth in a 3D model of the surfaces of the teeth and mandibular bone portion of the lower jaw of a patient in accordance with the present disclosure.

FIG. 13 illustrates movement of a tooth of the lower jaw in the 3D model of the teeth of the lower jaw (block 1007). As a frame of reference describing how the tooth can be moved, an arbitrary centerline (CL) may extend through the tooth. A set of orthogonal directions represented by references axes 1201, 1203, 1205 can be defined in reference to the centerline CL. The tooth can be moved in any one direction (or combination of directions) corresponding to the reference axes 1201, 1203, 1205. Furthermore, the tooth may be rotated about the axis 1205 (root angulation) or rotated about axis 1203 (torque), respectively. Additionally, the tooth may be rotated about the axis 1201. Thus, all possible free-form motions of the tooth can be performed. FIG. 13 further illustrates how the magnitude of tooth movement can be defined in terms of a maximum linear translation of any arbitrary point P on a tooth. Each point P will undergo a cumulative translation as that tooth is moved in any of the orthogonal or rotational directions defined in FIG. 13. That is, while the point will usually follow a nonlinear path, there is a linear distance between any point in the tooth when determined at different times during the treatment. Thus, the arbitrary point P may in fact undergo a true side-to-side translation as indicated by arrow d1, while a second arbitration point P2 may travel along an arcuate path, resulting in a final translation d2. Similar operations can be used to move the isolated mandibular bone part in the 3D model of the lower jaw. Here, all possible free-form motions of the mandibular bone part can be performed.

Figure 14:
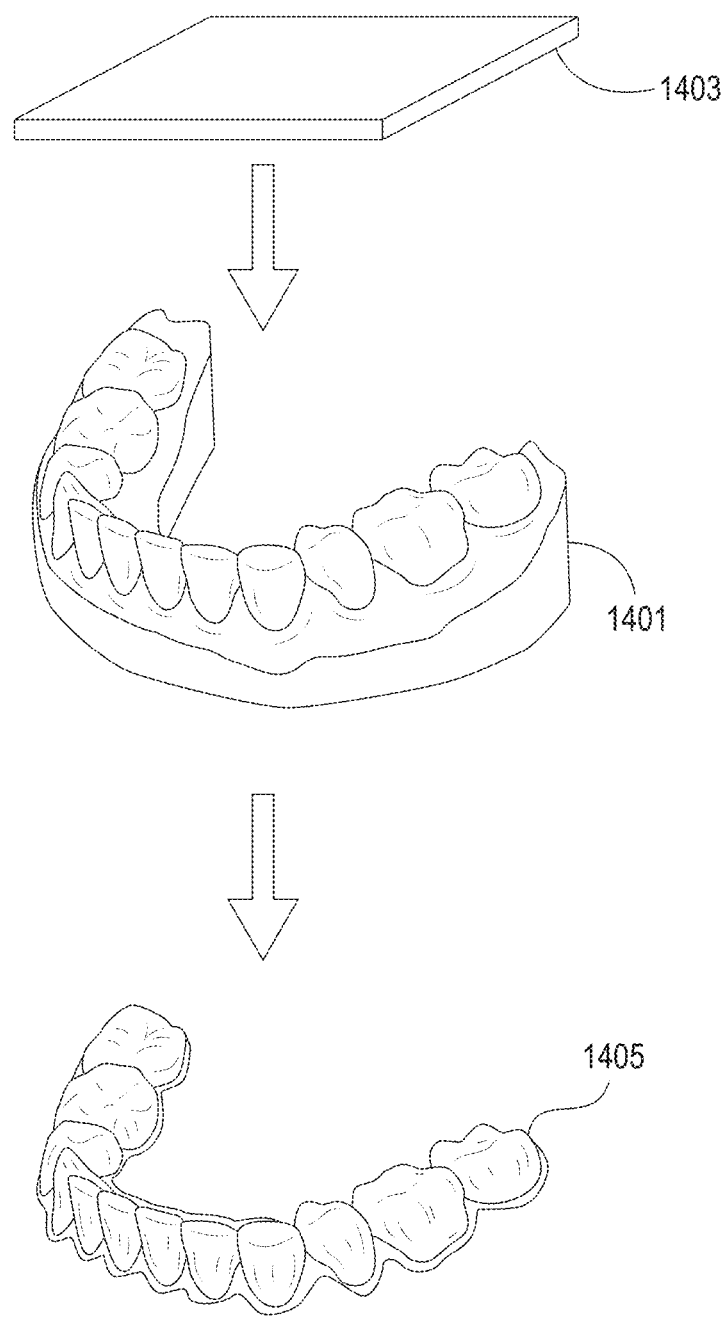
FIG. 14 is a schematic diagram illustrating operations that form a bottom aligner that covers the surfaces of the teeth and mandibular bone portion of the lower jaw of a patient in accordance with the present disclosure.
Figure 15A:
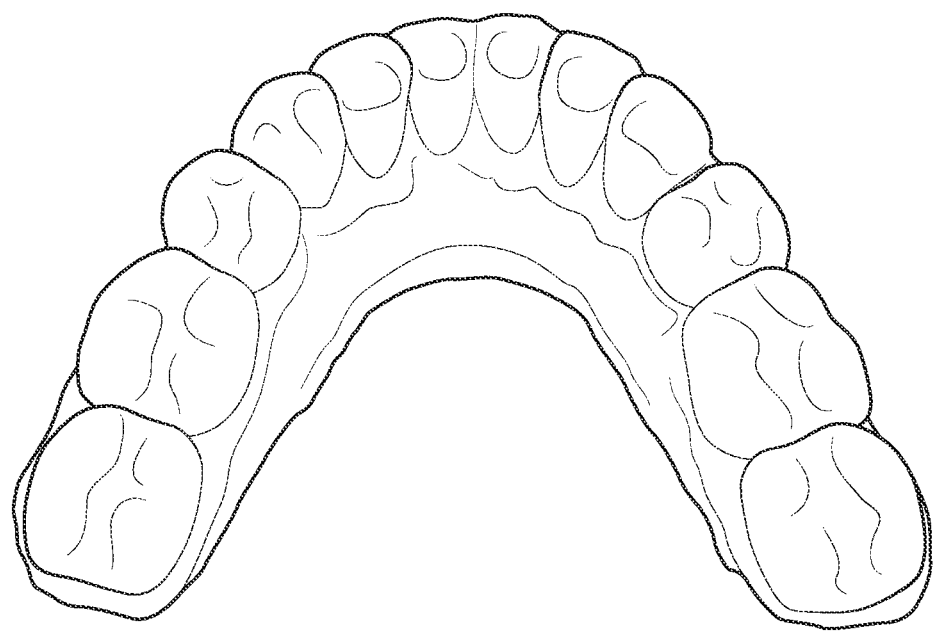
FIGS. 15A and 15B are schematic diagrams of exemplary bottom aligners in accordance with the present disclosure.
Figure 15B:
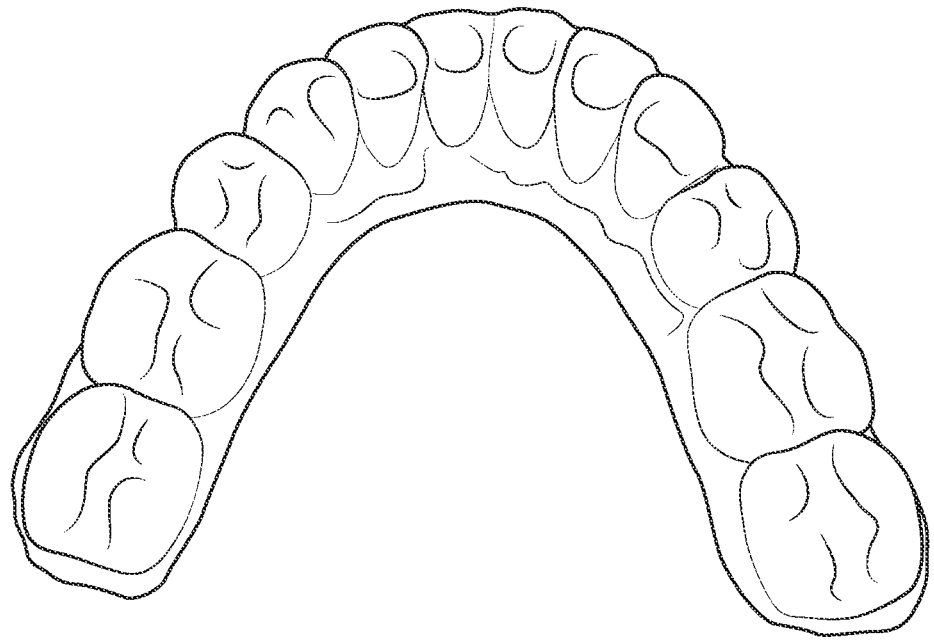

FIG. 14 illustrates the operations that create the bottom aligner (blocks 1017 and 1019). More specifically, the resultant 3D model (block 1013) can be used to generate a physical model (three-dimensional physical structure) 1401 representing the desired geometry of the surfaces of the teeth and the mandibular bone portion of the lower jaw of the patient. And the physical model 1401 can be used as a mold (e.g., positive mold) to mold a sheet of clear transparent polymeric material 1403 into the bottom aligner 1405. FIGS. 15A and 15B depict an exemplary bottom aligners formed by such operations.

Figure 16:
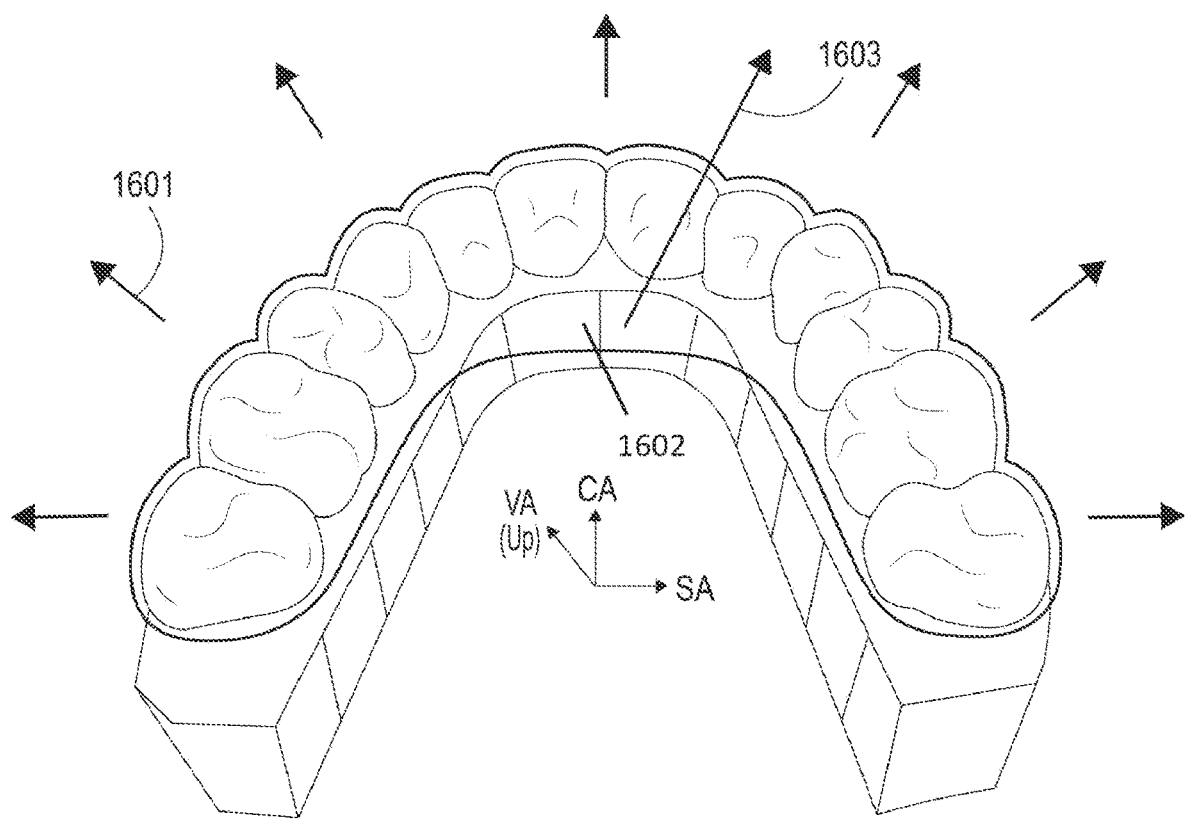
FIG. 16 is a schematic diagram illustrating exemplary corrective forces applied by a bottom aligner to the teeth and mandibular bone portion of the lower jaw of a patient in accordance with the present disclosure.

When worn by the user, the polymeric shell of the bottom aligner can apply corrective forces to all or only certain one(s) of the teeth of the lower jaw. The bottom aligner can also apply corrective forces to the mandibular bone portion of the lower jaw. The corrective forces can move or rotate the teeth and/or the mandibular bone portion in one or more desired directions or orientations as described herein. FIG. 16 illustrates an exemplary embodiment where the bottom aligner applies corrective forces that expand the lower jaw and move the teeth of the lower jaw outward as indicated by arrows 1601. In this configuration, the corrective forces expand the molars in the LR quadrant of the lower jaw (one shown corresponding to tooth 6 of the LR quadrant in FIG. 2) with a component in the outward direction (i.e., the SA direction toward the right side of the page). The corrective forces can also expand the molars in the LL quadrant of the lower jaw (one shown corresponding to tooth 6 of the LL quadrant in FIG. 2) with a component in the outward direction (i.e., the SA direction toward the left side of the page). The corrective forces can also expand the premolars and canine and lateral incisor in the LR quadrant of the lower jaw (four shown corresponding to teeth 5 to 2 in the LR quadrant in FIG. 2) with a component in the outward direction (i.e., the SA direction toward the right side of the page) and a component in the forward direction (i.e., the CA direction toward the top of the page). The corrective forces can also expand the premolars and canine and lateral incisor in the LL quadrant of the lower jaw (four shown corresponding to teeth 5 to 2 in the LL quadrant in FIG. 2) with a component in the outward direction (i.e., the SA direction toward the left side of the page) and a component in the forward direction (i.e., the CA direction toward the top of the page). The corrective forces can also expand the central incisors in the LR and LL quadrants of the lower jaw (two shown corresponding to tooth 1 in the LR and LL quadrants in FIG. 2) with a component in the forward direction (i.e., the CA direction toward the top of the page). The bottom aligner can also contact the mandibular bone portion disposed under the central incisors of the lower jaw and apply corrective forces that moves the mandibular bone portion 1602 disposed under the central incisors of the lower jaw outward (i.e., with components in the VA and CA directions) as indicated by arrow 1603. Such corrective forces can be used to correct for retrusion of the lower jaw as described herein.

In embodiments, the bottom aligner can be configured to move the teeth and/or mandibular bone portion of the lower jaw in a range of 0.1-0.3 mm. The typical movement can be 0.25 mm when the bottom aligner is worn for 2 weeks. However, the movement can be reduced to half or 0.125 mm and the bottom aligner is worn for 1 week. This creates a light, continuous force.

Furthermore, segments (or parts) of the teeth and/or mandibular bone portion of the lower jaw can be moved or stretched or transformed in a piecewise manner over varying directions and/or magnitudes over time if desired. For example, in one illustrative embodiment, the movement of the teeth of the lower jaw can be carried out in a sequence of three phases. In a first phase, the bottom aligner is configured to move the anterior teeth of the lower jaw (i.e., the incisors 1, 2 and canine 3 of FIG. 2) vertically downward to intrude the anterior teeth of the lower jaw. In a second phase that follows the first phase, another bottom aligner is configured to move the middle teeth of the lower jaw (i.e., the premolars 4,5 of FIG. 2) vertically downward to intrude the middle teeth of the lower jaw. In a third phase that follows the second phase, yet another bottom aligner is configured to move the back teeth of the lower jaw (i.e., the molars 6,7 of FIG. 2) vertically downward to intrude the back teeth of the lower jaw. In the third phase, the anterior teeth typically extrude back down to some degree due to the opposite force created by intruding the back teeth. This sequence of bottom aligners can be used to rotate the lower mandible vertically downward (in the VA (DOWN) direction) and forwards (in the CA direction).

In embodiments, the top aligner and bottom aligners as described herein can be configured such that the movement of the teeth of the upper jaw match that the movement (intrusion) of the teeth of the lower jaw (particularly, movement of the molars of the lower jaw) to align the bite contact between the teeth of the upper jaw and the teeth of the lower jaw.

In embodiments, retainers can be formed that conform to the shape and positioning of the upper and lower teeth of the patient. The retainers are worn on the upper and lower teeth of the patient after completion of orthodontic treatment and function to prevent movement of the upper and lower teeth. In one embodiment, one retainer is made for the teeth of the upper jaw, and another retainer is made for the teeth of the lower jaw. In another embodiment, the retainer made for the teeth of the upper jaw can be fused at the patient's occlusion to the retainer for the teeth of the lower jaw. This type of retainer prevents movement of the upper and lower teeth while helping keep the teeth together and mouth closed, especially when worn at night when sleeping.

In embodiments, the clinician and patient can employ a smartphone application (or web-based application) and related service to connect to one another for reviewing and revising the treatment plan for the patient.

In embodiments, the application and service can enable the clinician (i.e., orthodontist) to perform one or more of the following functions:

sign up by creating a profile for the clinician; for example, the clinician profile can include a Name, specialization information, address, and contact information store and edit the clinician profile (once initially created)

login/logout add patients treated by the clinician and related cases; this can involve generating a barcode that the patient has to scan store and view cases for patients treated by the clinician; for example, each case can include Case ID, link to a Patient Profile, and Treatment Information: for example, the treatment information can include a patient's progress graph, and images of the patient's teeth over time import and store images of patient's teeth message patients treated by the clinician check appointments requested by patients; for example, where the clinician can accept, decline, or propose new time receive notifications/messages from patients treated by the clinician manage notifications from patients treated by the clinician visualize progress of the treatment (movement of the teeth) for a patient treated by the clinician over time request a 3D scan of the patient's mouth (for example, if the once a week scan is used up) to performed by a patient treated by the clinician.

In embodiments, the application and service can also enable the patient to perform one or more of the following functions:

sign up by creating a profile for the patient; for example, the patient profile can include a Case ID, Name, Date of Birth, Contact Information, and Treatment Start Date store and edit the patient profile (once initially created)

login/logout add a clinician that is treating the patient; for example, by scanning a barcode supplied by the clinician perform a 3D scan of the patient's mouth, for example, a 3D scan of the teeth and palate of the upper jaw or a 3D scan of the teeth of the lower jaw;

store data representing the result of the 3D scan;

view data relating to movement of the teeth/palate based on result of the 3D scan of the patient's mouth send/share the results of the 3D scan of the patient's mouth and/or data relating to movement of the teeth/palate to the clinician that is treating the patient visualize progress of the treatment (movement of the teeth) by the clinician over time message the clinician that is treating the patient request an appointment with the clinician that is treating the patient view profile information for the clinician that is treating the patient receive notifications/messages from the clinician that is treating the patient manage notifications from the clinician that is treating the patient The 3D teeth scan(s) of the upper jaw of the patient obtained via the application and service can be used to generate one or more 3D models of the teeth and palate of the upper jaw for use in designing and creating one or more top aligners for the patient as described herein. Similarly, the 3D teeth scan(s) of the lower jaw of the patient obtained via the application and service can be used to generate one or more 3D models of the teeth of the lower jaw for use in designing and creating one or more bottom aligners for the patient as described herein.

FIG. 17 illustrates an example device 2500, with a processor 2502 and memory 2504 that can be configured to implement various embodiments of the present application. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a server computer, a virtual machine, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth). One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network. A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various systems and processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable, and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, general-purpose computer, special-purpose machine, virtual machine, software container, or appliance) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Some of the methods and processes described above, can be implemented as computer program logic for use with the computer processor. The computer program logic may be embodied in various forms, including a source code form or a computer executable form Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

There have been described and illustrated herein several embodiments of methods of systems for designing and fabricating orthodontic appliances as well as improved orthodontic appliances. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A method for repositioning teeth of a patient, comprising:
   providing at least one appliance specific to the patient for placement in the patient's mouth during use, wherein the at least one appliance comprises a polymeric shell having a cavity shaped to receive teeth of the upper jaw of the patient, the polymeric shell integral to a polymeric segment shaped to cover the hard palate of the upper jaw of the patient;
   wherein geometry of the shell is configured such that the at least one appliance adjusts position of the teeth of the upper jaw of the patient during use, and wherein geometry of the segment is configured such that the at least one appliance adjusts position of the hard palate of the upper jaw of the patient during use;
   wherein the geometry of the segment and the geometry of the shell for a particular appliance are derived from a three-dimensional model of surfaces of the teeth and hard palate of the upper jaw of the patient; and
   wherein the three-dimensional model of the surfaces of the teeth and hard palate of the upper jaw of the patient is generated by:
   i) isolating a tooth part of a three-dimensional model which corresponds to surfaces of at least one tooth of the upper jaw of the patient,
   ii) moving the isolated tooth part of the three-dimensional model such that the shell of the particular appliance is configured to expand the teeth of the upper jaw of the patient during use,
   iii) isolating a palate part of a three-dimensional model which corresponds to surfaces of the hard palate of the upper jaw of the patient, and
   iv) moving, stretching, or otherwise transforming the isolated palate part of the three-dimensional model such that the geometry of the segment of the particular appliance is configured to move the hard palate upward and forward during use.

2. A method according to claim 1, wherein:
   the at least one appliance specific to the patient comprises a plurality of appliances specific to the patient which are used in a predefined order by the patient, wherein the plurality of appliances are configured to progressively adjust position of the teeth and hard palate of the upper jaw of the patient.

3. A method according to claim 1, wherein:
   the three-dimensional model is used to generate a physical model of the upper jaw of the patient; and
   the physical model is used as a mold to form a particular appliance.

4. A method according to claim 1, wherein:
   the moving, stretching, or otherwise transforming the isolated palate part of the three-dimensional model involves translation or rotation or other movement of the isolated palate part of the three-dimensional model relative to a reference coordinate system defined in the three-dimensional model.

5. A method according to claim 1, further comprising:
   providing at least one additional appliance specific to the patient for placement in the patient's mouth during use, wherein the at least one additional appliance comprises a polymeric shell having a cavity shaped to receive teeth of the lower jaw of the patient, wherein geometry of the shell is configured such that the at least one additional appliance adjusts position of the teeth of the lower jaw of the patient during use.

6. A method according to claim 5, wherein:
   the at least one additional appliance includes a polymeric segment integral to the polymeric shell, wherein the polymeric segment is configured to contact a mandibular bone portion disposed below the gingiva of the teeth of the lower jaw and adjust position of the mandibular bone portion of the lower jaw of the patient during use.

7. A method according to claim 6, wherein:
   the geometries of the shell and segment for a particular additional appliance is derived from a three-dimensional model of surfaces of the teeth and mandibular bone portion of the lower jaw of the patient.

8. A method according to claim 6, wherein:
   the at least one additional appliance specific to the patient comprises a plurality of additional appliances specific to the patient which are used in a predefined order by the patient.

9. A method according to claim 8, wherein:
   the plurality of additional appliances are configured to progressively adjust position of the teeth and mandibular bone portion of the lower jaw of the patient.

10. A system for repositioning teeth of a patient, comprising:
    at least one appliance specific to the patient for placement in the patient's mouth during use, wherein the at least one appliance comprises a polymeric shell having a cavity shaped to receive teeth of the upper jaw of the patient, the polymeric shell integral to a polymeric segment shaped to cover the hard palate of the upper jaw of the patient, wherein geometry of the shell is configured such that the at least one appliance adjusts position of the teeth of the upper jaw of the patient during use, and wherein geometry of the segment is configured such that the at least one appliance adjusts position of the hard palate of the upper jaw of the patient during use; and
    at least one additional appliance specific to the patient for placement in the patient's mouth during use, wherein the at least one additional appliance comprises a polymeric shell having a cavity shaped to receive teeth of the lower jaw of the patient, wherein geometry of the shell is configured such that the at least one additional appliance adjusts position of the teeth of the lower jaw of the patient during use;
    wherein the at least one additional appliance includes a polymeric segment integral to the shell, wherein the segment is configured to contact a mandibular bone portion disposed below the gingiva of the teeth of the lower jaw, wherein geometry of the segment is configured such that the at least one additional appliance adjusts position of the mandibular bone portion of the lower jaw of the patient during use.

11. A system according to claim 10, wherein:
    the geometries of the shell and segment for a particular additional appliance is derived from a three-dimensional model of the surfaces of the teeth and mandibular bone portion of the lower jaw of the patient.

12. A system according to claim 10, wherein:
    the at least one additional appliance specific to the patient comprises a plurality of additional appliances specific to the patient which are used in a predefined order by the patient, wherein the plurality of additional appliances are configured to progressively adjust position of the teeth and mandibular bone portion of the lower jaw of the patient.

13. A system for repositioning teeth of a patient, comprising:
at least one appliance specific to the patient for placement in the patient's mouth during use, wherein the at least one appliance comprises a polymeric shell having a cavity shaped to receive teeth of the lower jaw of the patient and a polymeric segment integral to the shell, wherein the segment is configured to contact a mandibular bone portion disposed below the gingiva of the teeth of the lower jaw, wherein geometry of the shell is configured such that the at least one appliance adjusts position of the teeth of the lower jaw of the patient during use, and wherein geometry of the segment is configured such that the at least one appliance adjusts position of the mandibular bone portion of the lower jaw of the patient during use.

14. A system according to claim 13, wherein:
the at least one appliance specific to the patient comprises a plurality of appliances specific to the patient which are used in a predefined order by the patient, wherein the plurality of appliances are configured to progressively adjust position of the teeth and mandibular bone portion of the lower jaw of the patient.

15. A system according to claim 13, wherein:
the geometries of the shell and segment for a particular appliance is derived from a three-dimensional model of surfaces of the teeth and mandibular bone portion of the lower jaw of the patient.

16. A system according to claim 15, wherein:
the three-dimensional model of the surfaces of the teeth and mandibular bone portion of the lower jaw of the patient is generated by isolating a part of a three-dimensional model which corresponds to surfaces of the mandibular bone portion of the lower jaw of the patient, and moving, stretching, or otherwise transforming the isolated part of the three-dimensional model.

17. A system according to claim 15, wherein the three-dimensional model of the surfaces of the teeth and mandibular bone portion of the lower jaw of the patient is derived by:
i) generating an initial three-dimensional model representing surfaces of the teeth and a mandibular bone portion disposed below the gingiva of the lower jaw of a patient;
ii) isolating a tooth portion of the initial three-dimensional model which corresponds to surfaces of at least one tooth of the lower jaw of the patient;
iii) moving the tooth portion;
iv) isolating a mandibular bone part of the initial three-dimensional model which corresponds to surfaces of the mandibular bone portion of the lower jaw of the patient; and
v) moving, stretching, or otherwise transforming the mandibular bone part.

18. A system according to claim 17, wherein:
the moving, stretching, or otherwise transforming the mandibular bone part of v) involves distortion, translation or rotation or other movement of the mandibular bone part relative to a reference coordinate system defined in the initial three-dimensional model.

19. A system according to claim 17, wherein:
the moving, stretching, or otherwise transforming the mandibular bone part is configured such that the segment of the particular appliance moves the mandibular bone portion of the lower jaw outward to correct for retrusion of the lower jaw.

20. A method for repositioning teeth of a patient, comprising:
providing at least one appliance specific to the patient for placement in the patient's mouth during use, wherein the at least one appliance comprises a polymeric shell having a cavity shaped to receive teeth of the lower jaw of the patient and a polymeric segment integral to the shell, wherein the segment is configured to contact a mandibular bone portion disposed below the gingiva of the teeth of the lower jaw, wherein geometry of the shell is configured such that the at least one appliance adjusts position of the teeth of the lower jaw of the patient during use, and wherein geometry of the segment is configured such that the at least one appliance adjusts position of the mandibular bone portion of the lower jaw of the patient during use.

21. A method according to claim 20, wherein:
the at least one appliance specific to the patient comprises a plurality of appliances specific to the patient which are used in a predefined order by the patient, wherein the plurality of appliances are configured to progressively adjust position of the teeth and mandibular bone portion of the lower jaw of the patient.

22. A method according to claim 20, wherein:
the geometries of the shell and segment for a particular additional appliance is derived from a three-dimensional model of surfaces of the teeth and mandibular bone portion of the lower jaw of the patient.

23. A method according to claim 22, wherein:
the three-dimensional model of the surfaces of the teeth and mandibular bone portion of the lower jaw of the patient is generated by isolating a part of a three-dimensional model which corresponds to surfaces of the mandibular bone portion of the lower jaw of the patient, and moving, stretching, or otherwise transforming the isolated part of the three-dimensional model.

24. A method according to claim 23, wherein the three-dimensional model of the surfaces of the teeth and mandibular bone portion of the lower jaw of the patient is derived by:
i) generating an initial three-dimensional model representing surfaces of the teeth and a mandibular bone portion disposed below the gingiva of the lower jaw of a patient;
ii) isolating a tooth portion of the initial three-dimensional model which corresponds to surfaces of at least one tooth of the lower jaw of the patient;
iii) moving the tooth portion;
iv) isolating a mandibular bone part of the initial three-dimensional model which corresponds to surfaces of the mandibular bone portion of the lower jaw of the patient; and
v) moving, stretching, or otherwise transforming the mandibular bone part.

25. A method according to claim 24, wherein:
the moving, stretching, or otherwise transforming the mandibular bone part of v) involves distortion, translation or rotation or other movement of the mandibular bone part relative to a reference coordinate system defined in the initial three-dimensional model.

26. A method according to claim 24, wherein:
the moving, stretching, or otherwise transforming the mandibular bone part is configured such that the segment of the particular appliance moves the mandibular bone portion of the lower jaw outward to correct for retrusion of the lower jaw.

\* \* \* \* \*